(12) United States Patent
Kumar et al.

(10) Patent No.: US 11,795,238 B2
(45) Date of Patent: Oct. 24, 2023

(54) ANTI-IDIOTYPE ANTIBODIES TARGETING ANTI-CD70 CHIMERIC ANTIGEN RECEPTOR

(71) Applicant: CRISPR Therapeutics AG, Zug (CH)

(72) Inventors: Lalit Kumar, Cambridge, MA (US); Mary-Lee Dequeant, Cambridge, CA (US)

(73) Assignee: CRISPR Therapeutics AG, Zug (CH)

( * ) Notice: Subject to any disclaimer, the term of this patent is extended or adjusted under 35 U.S.C. 154(b) by 32 days.

(21) Appl. No.: 17/392,740

(22) Filed: Aug. 3, 2021

(65) Prior Publication Data

US 2022/0041754 A1    Feb. 10, 2022

Related U.S. Application Data

(60) Provisional application No. 63/060,838, filed on Aug. 4, 2020.

(51) Int. Cl.
*C07K 16/42* (2006.01)
*C07K 16/46* (2006.01)
*G01N 33/53* (2006.01)
*G01N 33/68* (2006.01)

(52) U.S. Cl.
CPC ..... *C07K 16/4266* (2013.01); *G01N 33/6854* (2013.01); *C07K 2317/76* (2013.01); *G01N 2333/70575* (2013.01)

(58) Field of Classification Search
None
See application file for complete search history.

(56) References Cited

PUBLICATIONS

[No Author Listed], GeneSeq Accession No. BGY89555. XP055853861. Dec. 26, 2019. 2 pages.
Jena et al., Chimeric antigen receptor (CAR)-specific monoclonal antibody to detect CD19-specific T cells in clinical trials. PLoS One. 2013;8(3):e57838(1-12), Epub Mar. 1, 2013.
Yvon et al., Immunotherapy of metastatic melanoma using genetically engineered GD2-specific T cells. Clin Cancer Res. Sep. 15, 2009;15(18):5852-60. Epub Sep. 8, 2009.

*Primary Examiner* — Maher M Haddad
(74) *Attorney, Agent, or Firm* — McDermott Will & Emery LLP

(57) ABSTRACT

High affinity antibodies capable of binding to a single-chain variable fragment (scFv) of anti-CD70 antibody, for example, the scFv expressed on cell surface as a portion of a chimeric antigen receptor (CAR). Also provided herein are methods for producing such anti-scFv antibodies and methods of using the antibodies disclosed herein for detecting, for example, T cells expressing an anti-CD70 CAR that comprise the scFv as an extracellular domain.

20 Claims, 3 Drawing Sheets
Specification includes a Sequence Listing.

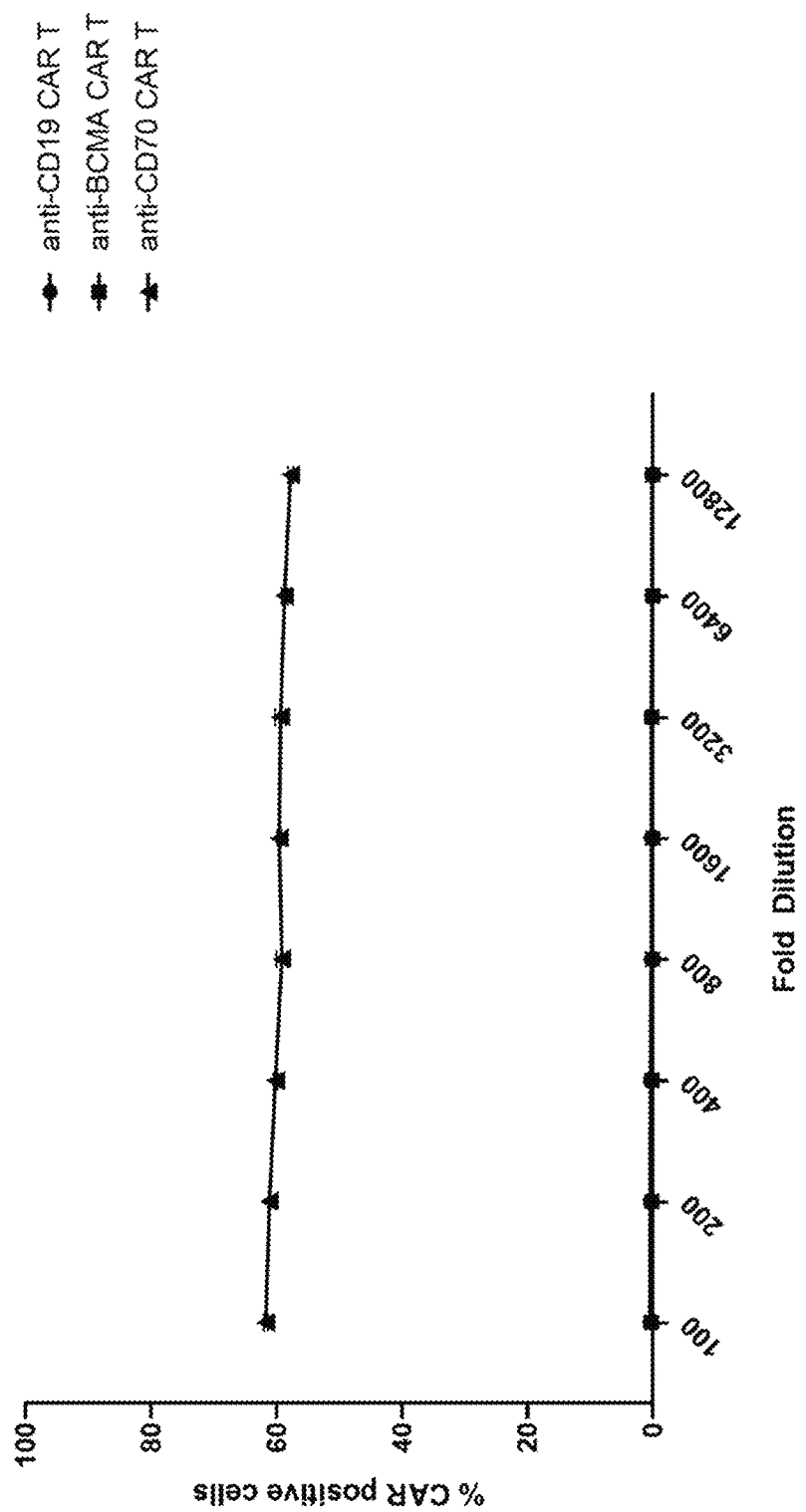

ANTI-IDIOTYPE ANTIBODIES TARGETING ANTI-CD70 CHIMERIC ANTIGEN RECEPTOR

CROSS REFERENCE TO RELATED APPLICATIONS

This application claims the benefit of the filing dates of U.S. Provisional Application No. 63/060,838, filed Aug. 4, 2020, the entire contents of which are incorporated by reference herein.

SEQUENCE LISTING

The application contains a Sequence Listing that has been filed electronically in the form of a text file, created Aug. 3, 2021 and named "095136-0361-025US1_SeqListing.txt" (32,097 bytes), the contents of which are incorporated by reference herein in their entirety

BACKGROUND

Chimeric antigen receptor (CAR) T-cell therapy has shown promising therapeutic effects in cancer treatment. Typically, CAR-T cells are generated by genetic engineering of either patient immune cells (autologous) or immune cells from human donors (allogenic). Production of high-quality, clinical grade CAR-T cells is a prerequisite for the wide application of this technology. It is therefore of great interest to develop tools for detecting CAR-expressing T cells.

SUMMARY

The present disclosure is based, at least in part, on the development of antibodies having high binding affinity and specificity to a single-chain variable fragment (scFv) of mouse anti-human CD70 antibody (SEQ ID NO:1), particularly to the scFv expressed on a cell surface. For example, antibody 20H05-2D09 disclosed herein displayed high binding affinity and specificity to T cells expressing an anti-CD70 chimeric receptor (anti-CD70 CAR) having the scFv of SEQ ID NO:1 as the extracellular domain.

Accordingly, the present disclosure provides, in some aspects, an isolated antibody, which binds a single-chain variable fragment (scFv) consisting of the amino acid sequence of SEQ ID NO: 1 (anti-scFv antibody). In some instances, the anti-scFv antibody binds the same epitope of the scFv as antibody 20H05-2D09 or competes against antibody 20H05-2D09 for binding to the scFv. In some embodiments, the isolated antibody binds the scFv expressed on a cell surface, for example, as the extracellular domain of a chimeric antigen receptor.

In some embodiments, the isolated antibody comprises the same heavy chain complementary determining regions and the same light chain complementary determining regions as exemplary antibody 20H05-2D09. For example, the isolated antibody may comprise the same heavy chain variable region ($V_H$) and the same light chain variable region ($V_L$) as antibody 20H05-2D09.

Any of the anti-scFv antibodies disclosed herein may be full-length antibodies. Alternatively, the anti-scFv antibodies may be an antigen-binding fragment.

In addition, the present disclosure features a nucleic acid or a set of nucleic acids (two individual nucleic acid molecules), which collectively encodes any of the anti-scFv antibodies described herein. In some embodiments, the nucleic acid or the set of nucleic acids is a vector or a set of vectors, for example, an expression vector(s).

Also provided herein is a host cell comprising the nucleic acid or the set of nucleic acids coding for any of the anti-scFv antibodies disclosed herein. In some embodiments, the host cell is a mammalian cell.

In other aspects, the present disclosure features a method for detecting or quantifying a single-chain variable fragment (scFv) that consists of the amino acid sequence of SEQ ID NO: 1. Such a method may comprise: (i) contacting an anti-scFv antibody as disclosed herein (e.g., an antibody having the same heavy chain and light chain CDRs or the same $V_H$ and $V_L$ chains as exemplary antibody 20H05-2D09 with a sample suspected of containing the scFv of SEQ ID NO:1, and (ii) detecting binding of the antibody to the scFv. In some embodiments, the scFv is the extracellular domain of an anti-CD70 chimeric antigen receptor (CAR) expressed on a cell surface. In some embodiments, the anti-scFv antibody can be conjugated to a detectable label.

In some embodiments, the sample may comprise a plurality of T cells, which are genetically engineered to express an anti-CD70 CAR that comprises the scFv of SEQ ID NO:1 as the extracellular domain. In some embodiments, the plurality of T cells may further comprise a disrupted TRAC gene, a disrupted β2M gene, or both. In some examples, the plurality of T cells are prepared from T cells obtained from one or more donors.

In some instances, the sample is derived from a manufacturing process for producing the plurality of T cells that are genetically engineered for expressing the anti-CD70 CAR.

In some embodiments, the sample is a biological sample obtained from a subject administered a plurality of T cells, which are genetically engineered to express the anti-CD70 CAR. In some examples, the biological sample is a blood sample. In other examples, the biological sample is a tissue sample. The subject may be a human cancer patient, for example, a human cancer patient having a relapsed or refractory B-cell malignancy. Exemplary B-cell malignancy includes, but is not limited to, non-Hodgkin lymphoma or B-cell lymphoma. Alternatively or in addition, the subject may be a human cancer patient, for example, a human cancer patient having a CD70+ solid tumor. Exemplary CD70+ solid tumor includes, but is not limited to, a renal cell carcinoma (RCC), a lung cancer, a gastric cancer, an ovarian cancer, a pancreatic cancer, a prostate cancer, and/or a combination thereof.

Further, the present disclosure provides a method of producing any of the anti-scFv antibodies disclosed herein. The method may comprise: (i) culturing any of the host cells described herein that comprise one or more nucleic acids encoding the anti-scFv antibody under conditions allowing for expression of the antibody that binds the scFv; and (ii) harvesting the antibody thus produced from the cell culture. In some embodiments, the method may further comprise (iii) purifying the antibody after step (ii).

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to the drawing in combination with the detailed description of specific embodiments presented herein.

FIG. 2 is a diagram showing that antibody clone 20H05-02D09 binds specifically to anti-CD70 CAR T cells (CAR T cells that express a CAR containing the anti-CD70-scFv), but not anti-BCMA CAR T cells or anti-CD19 CAR T cells.

DETAILED DESCRIPTION

Figure 1A:
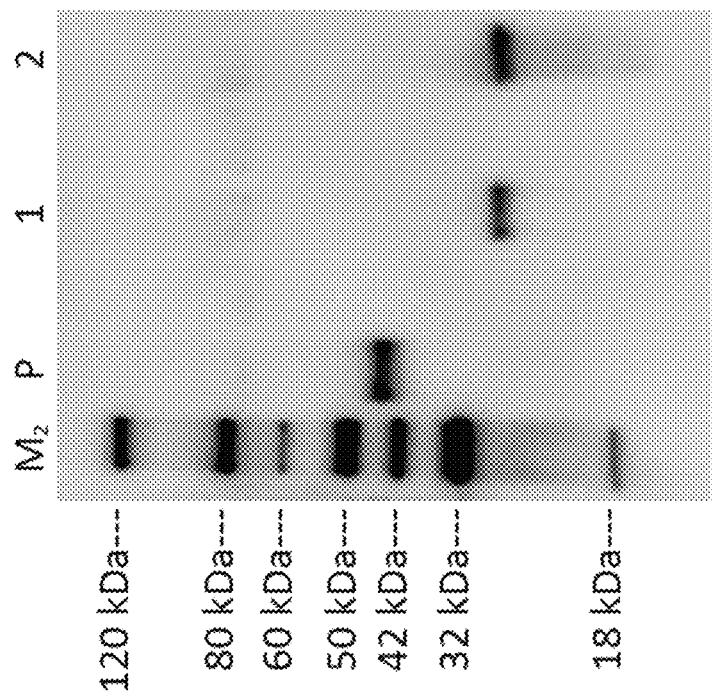
FIGS. 1A-1B are photos showing production of recombinant an anti-CD70-scFv protein analyzed by SDS-PAGE (FIG. 1A) and Western-blot analysis (FIG. 1B). Lane $M_1$: Protein Marker (Takara Bio USA, Mountain View, Calif., Cat. No. 3452). Lane $M_2$: Protein Marker (GenScript Biotech, Piscataway, N.J., Cat. No. M00521). Lane 1: Reducing conditions. Lane 2: Non-reducing conditions. Lane P: Multiple-tag (GenScript Biotech, Piscataway, N.J., Cat. No. M0101) as a positive control. Primary antibody: Mouse-anti-His mAb (GenScript Biotech, Piscataway, N.J., Cat. No. A00186).

Provided herein are antibodies capable of binding to an anti-CD70 single-chain variable fragment (scFv) having the amino acid sequence of SEQ ID NO:1, e.g., capable of binding to the scFv expressed on cell surface as the extracellular domain of an anti-CD70 chimeric antigen receptor (CAR). As such, the antibodies disclosed herein may be used for detecting presence of cells (e.g., T cells) expressing such an anti-CD70 CAR in a sample, e.g., samples obtained from a manufacturing process for producing anti-CD70 CAR-T cells or samples obtained from patients who are administered anti-CD70 CAR-T cells.

I. Antibodies Binding to Anti-CD70 Single-Chain Variable Fragment (scFv)

The present disclosure provides antibodies (e.g., antibody 20H05-02D09) binding to a single-chain variable fragment (scFv) having the amino acid sequence of SEQ ID NO: 1 (provided below), which comprises the heavy chain variable domain ($V_H$) and light chain variable domain ($V_L$) derived from a mouse anti-human CD70 antibody. As such, the antibodies provided herein may be referred to as anti-scFv antibodies or anti-idiotypic (anti-ID) antibodies. In some embodiments, the antibodies disclosed herein are capable of binding to the scFv expressed on a cell surface. In specific examples, the antibodies disclosed herein bind to a cell-surface expressed anti-CD70 chimeric antigen receptor (CAR) comprising the scFv of SEQ ID NO:1 as the extracellular domain. The linker fragment is in boldface.

```
Amino Acid Sequence of the scFv Antigen (SEQ ID
NO: 1):
                                      (SEQ ID NO: 1)
QVQLVQSGAEVKKPGASVKVSCKASGYTFTNYGMNWVRQAPGQGLKWMGW

INTYTGEPTYADAFKGRVTMTRDTSISTAYMELSRLRSDDTAVYYCARDY

GDYGMDYWGQGTTVTVSSGGGGSGGGGSGGGGSGDIVMTQSPDSLAVSLG

ERATINCRASKSVSTSGYSFMHWYQQKPGQPPKLLIYLASNLESGVPDRF

SGSGSGTDFTLTISSLQAEDVAVYYCQHSREVPWTFGQGTKVEIK
```

An antibody (interchangeably used in plural form) is an immunoglobulin molecule capable of specific binding to a target, such as the scFv of SEQ ID NO:1 in the present application, through at least one antigen recognition site, located in the variable region of the immunoglobulin molecule. As used herein, the term "antibody" encompasses not only intact (e.g., full-length) polyclonal or monoclonal antibodies, but also antigen-binding fragments thereof (such as Fab, Fab', F(ab')2, Fv), single-chain antibody (scFv), fusion proteins comprising an antibody portion, humanized antibodies, chimeric antibodies, diabodies, single domain antibody (e.g., nanobody), single domain antibodies (e.g., a $V_H$ only antibody), multispecific antibodies (e.g., bispecific antibodies) and any other modified configuration of an immunoglobulin molecule that comprises an antigen recognition site of the required specificity, including glycosylation variants of antibodies, amino acid sequence variants of antibodies, and covalently modified antibodies. An antibody as disclosed herein includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, E. A., et al. (1991) *Sequences of Proteins of Immunological Interest*, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs.

The anti-scFv antibodies described herein may be a full-length antibody, which contains two heavy chains and two light chains, each including a variable domain and a constant domain. Alternatively, the anti-scFv antibodies described herein can be an antigen-binding fragment of a full-length antibody. Examples of binding fragments encompassed within the term "antigen-binding fragment" of a full length antibody include (i) a Fab fragment, a monovalent fragment consisting of the $V_L$, $V_H$, $C_L$ and $C_H1$ domains; (ii) a F(ab')$_2$ fragment, a bivalent fragment including two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) that retains functionality. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv). See e.g., Bird et al. (1988) *Science* 242:423-426; and Huston et al. (1988) *Proc. Natl. Acad. Sci. USA* 85:5879-5883.

The anti-scFv antibodies described herein can be of a suitable origin, for example, murine, rat, or human. Such antibodies are non-naturally occurring, i.e., would not be produced in an animal without human act (e.g., immunizing such an animal with a desired antigen or fragment thereof or isolated from antibody libraries). Any of the anti-scFv antibodies described herein, e.g., antibody 20H05-02D09, can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In some embodiments, the anti-scFv antibodies described herein are human antibodies, which may be isolated from a human antibody library or generated in transgenic mice. For example, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Amgen, Inc. (Fremont, Calif.) and HuMAb-Mouse™ and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) *Annu. Rev. Immunol.* 12:433-455. Alternatively, the antibody library display technology, such as phage, yeast display, mammalian cell display, or mRNA display technology as known in the art can be used to produce human antibodies and antibody fragments in vitro, from immunoglobulin variable (V) domain gene repertoires from unimmunized donors.

In other embodiments, the anti-scFv antibodies described herein may be humanized antibodies or chimeric antibodies. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. In general, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, one or more Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In some instances, the humanized antibody may comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, or six) which are altered with respect to the original antibody, which are also termed one or more CDRs "derived from" one or more CDRs from the original antibody. Humanized antibodies may also involve affinity maturation. Methods for constructing humanized antibodies are also well known in the art. See, e.g., Queen et al., Proc. Natl. Acad. Sci. USA, 86:10029-10033 (1989).

In some embodiments, the anti-scFv antibodies described herein can be a chimeric antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region. Techniques developed for the production of "chimeric antibodies" are well known in the art. See, e.g., Morrison et al. (1984) *Proc. Natl. Acad. Sci. USA* 81, 6851; Neuberger et al. (1984) *Nature* 312, 604; and Takeda et al. (1984) *Nature* 314:452.

In some embodiments, the anti-scFv antibodies described herein specifically bind to the corresponding target antigen (i.e., the anti-CD70 scFv of SEQ ID NO: 1 or a polypeptide such as a chimeric antigen receptor comprising such) or an epitope thereof. An antibody that "specifically binds" to an antigen or an epitope is a term well understood in the art. A molecule is said to exhibit "specific binding" if it reacts more frequently, more rapidly, with greater duration, with greater avidity, and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen (i.e., only baseline binding activity can be detected in a conventional method).

In some embodiments, the anti-scFv antibodies described herein (e.g., antibody 20H05-02D09) have a suitable binding affinity for the target antigen (i.e., the anti-CD70 scFv of SEQ ID NO: 1 or a polypeptide such as a chimeric antigen receptor comprising such) or antigenic epitopes thereof. As used herein, "binding affinity" refers to the apparent association constant or $K_A$. The $K_A$ is the reciprocal of the dissociation constant ($K_D$). The antibody described herein may have a binding affinity ($K_D$) of at least 100 mM, 10 mM, 1 mM, 0.1 mM, 100 μM, 10 μM, 1 μM, 0.1 μM, 100 nM, 10 nM, 1 nM, 0.1 nM, or lower for the scFv from antibody FMC63. An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 90, 100, 500, 1000, 10,000 or $10^5$ fold. In some embodiments, any of the antibodies disclosed herein may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

$$[Bound]=[Free]/(Kd+[Free])$$

It is not always necessary to make an exact determination of $K_A$, since sometimes it is sufficient to obtain a quantitative measurement of affinity (e.g., determined using a method such as ELISA or FACS analysis), which is proportional to $K_A$. The quantitative measurement thus can be used for comparisons, such as determining whether a higher affinity is, e.g., 2-fold higher, so as to obtain a qualitative measurement of affinity, or to obtain an inference of affinity, e.g., by activity in a functional assay, e.g., an in vitro or in vivo assay.

The structural information (heavy chain and light chain variable domains) of an exemplary antibody 20H05-02D09 is provided below. The heavy chain CDRs and light chain CDRs (determined by the Kabat approach; see, e.g., Kabat, E. A., et al. (1991) *Sequences of Proteins of Immunological Interest*, Fifth Edition, U.S. Department of Health and Human Services, NIH Publication No. 91-3242, imgt.org/IMGTindex/V-QUEST.php, and ncbi.nlm.nih.gov/igblast/) are identified in boldface. See also Table 6 below.

TABLE 1

$V_H$ and $V_L$ Sequences of anti-scFv antibody 20H05-02D09.

| Description | SEQ ID NO: | Sequences (CDRs in boldface) |
|---|---|---|
| Heavy chain variable ($V_H$) | 2 | QIQLVQSGPELKKPGETVKISCKASGYTFTNYGMH WVKQAPGKVLKWMGWINTYSGVPTYPDDFKGRFAF SLETSASTASLQINNLKNEDTATYFCATERLRGWF PFWGQGTLVTVSA |

TABLE 1-continued $V_H$ and $V_L$ Sequences of anti-scFv antibody 20H05-02D09.

| Description | SEQ ID NO: | Sequences (CDRs in boldface) |
|---|---|---|
| Light chain variable ($V_L$) | 3 | QIVLTQSPAIMSASPGEKVTISCSASSSVSYMYWY QQKPGSSPKPWIYRTSNLASGVPARFSGSGSGTSY SLTISSMEAEDAATYYCQQYHSYPPTFGGGTKLEI K |

In some embodiments, the anti-scFv antibodies described herein bind to the same epitope in SEQ ID NO: 1 as the exemplary antibody 20H05-02D09 or compete against the exemplary antibody for binding to the scFv antigen (SEQ ID NO:1). An "epitope" as used herein refers to the site on a target antigen that is recognized and bound by an antibody. The site can be entirely composed of amino acid components, entirely composed of chemical modifications of amino acids of the protein (e.g., glycosyl moieties), or composed of combinations thereof. Overlapping epitopes include at least one common amino acid residue. An epitope can be linear, which is typically 6-15 amino acids in length. Alternatively, the epitope can be conformational. The epitope to which an antibody binds can be determined by routine technology, for example, the epitope mapping method (see, e.g., descriptions below). An antibody that binds the same epitope as an exemplary antibody described herein may bind to exactly the same epitope or a substantially overlapping epitope (e.g., containing less than 3 non-overlapping amino acid residues, less than 2 non-overlapping amino acid residues, or only 1 non-overlapping amino acid residue) as the exemplary antibody. Whether two antibodies compete against each other for binding to the cognate antigen can be determined by a competition assay, which is well known in the art.

In some examples, the anti-scFv antibodies disclosed herein comprises the same $V_H$ and/or $V_L$ CDRs as the exemplary antibody 20H05-02D09. Two antibodies having the same $V_H$ and/or $V_L$ CDRs means that their CDRs are identical when determined by the same approach (e.g., the Kabat approach, the Chothia approach, the AbM approach, the Contact approach, or the IMGT approach as known in the art. See, e.g., bioinf.org.uk/abs/). Such antibodies may have the same $V_H$, the same $V_L$, or both as compared to an exemplary antibody described herein. The heavy chain and light chain CDRs of exemplary antibody 20H05-02D09, determined by the various approaches as noted, are provided in Table 6 below. For example, the antibody disclosed herein, in some instances, comprises the heavy chain CDRs set forth in SEQ ID NOs:9-11 and light chain CDRs set forth in SEQ ID NOs:15-17 following the Kabat approach. In other examples, the antibody disclosed herein comprises the heavy chain CDRs set forth in SEQ ID NOs:12-14 and light chain CDRs set forth in SEQ ID NO:18, RTS, and SEQ ID NO:17 following the Chothia approach.

Also within the scope of the present disclosure are functional variants of exemplary antibody 20H05-02D09. Such functional variants are substantially similar to the exemplary antibody, both structurally and functionally. A functional variant comprises substantially similar $V_H$ and $V_L$ CDRs as the exemplary antibody. For example, it may comprise only up to 8 (e.g., 8, 7, 6, 5, 4, 3, 2, or 1) amino acid residue variations in the total CDR regions of the antibody and binds the same epitope in SEQ ID NO: 1 with substantially similar affinity (e.g., having a $K_D$ value in the same order). In some instances, the functional variants may have the same heavy chain CDR3 as the exemplary antibody, and optionally the same light chain CDR3 as the exemplary antibody. Alternatively or in addition, the functional variants may have the same heavy chain CDR2 as the exemplary antibody. Such an antibody may comprise a $V_H$ fragment having CDR amino acid residue variations in only the heavy chain CDR1 as compared with the $V_H$ of the exemplary antibody. In some examples, the antibody may further comprise a $V_L$ fragment having the same $V_L$ CDR3, and optionally the same $V_L$ CDR1 or VL CDR2 as the exemplary antibody.

In some instances, the amino acid residue variations (e.g., in one or more of the heavy chain and light chain CDRs of antibody 20H05-02D09) can be conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D.

In some embodiments, the anti-scFv antibodies disclosed herein may comprise heavy chain CDRs that are at least 80% (e.g., 85%, 90%, 95%, or 98%) identical, individually or collectively, as compared with the $V_H$ CDRs of the exemplary antibody 20H05-02D09. Alternatively or in addition, the anti-scFv antibodies disclosed herein may comprise light chain CDRs that are at least 80% (e.g., 85%, 90%, 95%, or 98%) identical, individually or collectively, as compared with the $V_L$ CDRs as the exemplary antibody 20H05-02D09. As used herein, "individually" means that one CDR of an antibody shares the indicated sequence identity relative to the corresponding CDR of the exemplary antibody. "Collectively" means that three $V_H$ or $V_L$ CDRs of an antibody in combination share the indicated sequence identity relative the corresponding three $V_H$ or $V_L$ CDRs of the exemplary antibody in combination.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some embodiments, the heavy chain of any of the anti-scFv antibodies as described herein may further comprise a heavy chain constant region (CH) or a portion thereof (e.g., CH1, CH2, CH3, or a combination thereof). The heavy chain constant region can of any suitable origin, e.g., human, mouse, rat, or rabbit. Alternatively or in addition, the light chain of the antibody may further comprise a light chain constant region (CL), which can be any CL known in the art. In some examples, the CL is a kappa light chain. In other examples, the CL is a lambda light chain. Antibody heavy and light chain constant regions are well known in the art, e.g., those provided in the IMGT database (www.imgt.org) or at www.vbase2.org/vbstat.php., both of which are incorporated by reference herein.

II. Preparation of Anti-Single-Chain Variable Fragment (scFv) Antibodies

The anti-scFv antibodies described herein (e.g., antibody 20H05-02D09) can be made by any method known in the art. See, for example, Harlow and Lane, (1998) Antibodies: A Laboratory Manual, Cold Spring Harbor Laboratory, New York.

In some embodiments, the anti-scFv antibody may be produced by the conventional hybridoma technology. The full-length anti-CD70 scFv antigen of SEQ ID NO: 1 or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-scFv monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as a source of antibodies encompasses all derivatives, progeny cells of the parent hybridomas that produce monoclonal antibodies capable of binding to SEQ ID NO: 1. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N═C═NR, where R and R1 are different alkyl groups, can yield a population of antibodies (e.g., monoclonal antibodies).

If desired, an antibody (monoclonal or polyclonal) of interest (e.g., produced by a hybridoma cell line) may be sequenced and the polynucleotide sequence may then be cloned into a vector for expression or propagation. The sequence encoding the antibody of interest may be maintained in the vector in a host cell and the host cell can then be expanded and frozen for future use. In an alternative, the polynucleotide sequence may be used for genetic manipulation to, e.g., humanize the antibody or to improve the affinity (affinity maturation), or other characteristics of the antibody. For example, the constant region may be engineered to more resemble human constant regions to avoid immune response if the antibody is from a non-human source and is to be used in clinical trials and treatments in humans. Alternatively, or in addition, it may be desirable to genetically manipulate the antibody sequence to obtain greater affinity and/or specificity to the target antigen. It will be apparent to one of skill in the art that one or more polynucleotide changes can be made to the antibody and still maintain its binding specificity to the target antigen.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibody specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen, in which various fragments of the single-chain variable fragment (scFv) protein have been replaced (swapped) with sequences from a closely related, but antigenically distinct protein. By assessing binding of the antibody to the mutant scFv polypeptide, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

In some embodiments, the anti-scFv antibodies disclosed herein can be produced using the conventional recombinant technology as exemplified below.

Nucleic acids encoding the heavy and light chain of an antibody described herein can be cloned into one expression vector, each nucleotide sequence being in operable linkage to a suitable promoter. In one example, each of the nucleotide sequences encoding the heavy chain and light chain is in operable linkage to a distinct prompter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters (Brown, M. et al., Cell, 49:603-612 (1987)), those using the tetracycline repressor (tetR) (Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)). Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters (M. Brown et al., Cell, 49:603-612 (1987)); Gossen and Bujard (1992); (M. Gossen et al., Natl. Acad. Sci. USA, 89:5547-5551 (1992)) combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy, 10(11):1811-1818, 1999). One particular advantage of this tetracycline inducible switch is that it does not require the use of a tetracycline repressor-mammalian cells transactivator or repressor fusion protein, which in some instances can be toxic to cells (Gossen et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an antibody described herein. The recombinant expression vector can be introduced into a suitable host cell (e.g., a dhfr− CHO cell) by a conventional method, e.g, calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of an antibody described herein (e.g., antibody 20H05-02D09) and the other encoding the light chain of the antibody described herein (e.g., antibody 20H05-02D09). Both of the two recombinant expression vectors can be introduced into a suitable host cell (e.g., dhfr− CHO cell) by a conventional method, e.g., calcium phosphate-mediated transfection. Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-scFv antibody as described herein (e.g., antibody 20H05-02D09), vectors (e.g., expression vectors) containing such, and host cells comprising the vectors are within the scope of the present disclosure.

In other embodiments, the anti-scFv antibodies described herein can be single-chain antibody fragments (scFv). A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to a single-chain variable fragment (scFv) of SEQ ID NO: 1, which can be identified from the library following routine procedures. Positive clones can be subjected to further screening to identify those that bind the scFv of SEQ ID NO: 1.

III. Applications of Anti-Single-Chain Variable Fragment (scFv) Antibodies

The present disclosure also provides methods for detecting or quantifying a single-chain variable fragment (scFv) consisting of the amino acid sequence of SEQ ID NO: 1 (specific to CD70) in a sample using any of the anti-scFv antibodies as described herein (e.g., antibody 20H05-02D09). To perform the method disclosed herein, any of the anti-scFv antibodies can be brought in contact with a sample suspected of containing a target antigen as disclosed herein—the anti-CD70 scFv of SEQ ID NO:1 or a polypeptide such as a CAR construct comprising such. In general, the term "contacting" or "in contact" refers to an exposure of the anti-scFv antibody disclosed herein with the sample suspected of containing the target antigen for a suitable period under suitable conditions sufficient for the formation of a complex between the anti-scFv antibody and the target antigen in the sample, if any. In some embodiments, the contacting is performed by capillary action in which a sample is moved across a surface of the support membrane. The antibody-antigen complex thus formed, if any, can be determined via a routine approach. Detection of such an antibody-antigen complex after the incubation is indicative of the presence of the target antigen in the sample. When needed, the amount of the antibody-antigen complex can be quantified, which is indicative of the level of the target antigen in the sample.

In some embodiments, a target antigen disclosed herein (i.e., the anti-CD70 scFv of SEQ ID NO:1 or a polypeptide comprising such) in a sample can be detected or quantified using any of the anti-scFv antibodies disclosed herein via an immunoassay. Examples of immunoassays include, without limitation, immunoblotting assay (e.g., Western blot), immunohistochemical analysis, flow cytometry assay, immunofluorescence assay (IF), enzyme linked immunosorbent assays (ELISAs) (e.g., sandwich ELISAs), radioimmunoassays, electrochemiluminescence-based detection assays, magnetic immunoassays, lateral flow assays, and related techniques. Additional suitable immunoassays for detecting the target antigen in a sample will be apparent to those of skill in the art.

In some examples, the anti-scFv antibodies as described herein (e.g., antibodies comprising the same heavy chain and light chain CDRs or comprising the same $V_H$ and the same $V_L$ as antibody 20H05-02D09) can be conjugated to a detectable label, which can be any agent capable of releasing a detectable signal directly or indirectly. The presence of such a detectable signal or intensity of the signal is indicative of presence or quantity of the target antigen in the sample. Alternatively, a secondary antibody specific to the anti-scFv antibody or specific to the target antigen may be used in the methods disclosed herein. For example, when the anti-scFv antibody used in the method is a full-length antibody, the secondary antibody may bind to the constant region of the anti-scFv antibody. In other instances, the secondary antibody may bind to an epitope of the target antigen that is different from the binding epitope of the anti-scFv antibody. Any of the secondary antibodies disclosed herein may be conjugated to a detectable label.

Any suitable detectable label known in the art can be used in the assay methods described herein. In some embodiments, a detectable label can be a label that directly releases a detectable signal. Examples include a fluorescent label or a dye. A fluorescent label comprises a fluorophore, which is a fluorescent chemical compound that can re-emit light upon light excitation. Examples of fluorescent label include, but are not limited to, xanthene derivatives (e.g., fluorescein, rhodamine, Oregon green, eosin, and Texas red), cyanine derivatives (e.g., cyanine, indocarbocyanine, oxacarbocyanine, thiacarbocyanine, and merocyanine), squaraine derivatives and ring-substituted squaraines (e.g., Seta and Square dyes), squaraine rotaxane derivatives such as SeTau dyes, naphthalene derivatives (e.g., dansyl and prodan derivatives), coumarin derivatives, oxadiazole derivatives (e.g., pyridyloxazole, nitrobenzoxadiazole and benzoxadiazole), anthracene derivatives (e.g., anthraquinones, including DRAQ5, DRAQ7 and CyTRAK Orange), pyrene derivatives such as cascade blue, oxazine derivatives (e.g., Nile red, Nile blue, cresyl violet, and oxazine 170), acridine derivatives (e.g., proflavin, acridine orange, and acridine yellow), arylmethine derivatives (e.g., auramine, crystal violet, and malachite green), and tetrapyrrole derivatives (e.g., porphin, phthalocyanine, and bilirubin). A dye can be a molecule comprising a chromophore, which is responsible for the color of the dye. In some examples, the detectable label can be fluorescein isothiocyanate (FITC), phycoerythrin (PE), Allophycocyanin (APC) or Alexa Fluor® 488.

In some embodiments, the detectable label may be a molecule that releases a detectable signal indirectly, for example, via conversion of a reagent to a product that directly releases the detectable signal. In some examples, such a detectable label may be an enzyme (e.g., β-galactosidase, HRP or AP) capable of producing a colored product from a colorless substrate.

In some embodiments, the detectable label may be a member of a receptor-ligand pair, which refers to a pair of molecules capable of binding to each other with high binding affinity and specificity. A secondary antibody conjugated to the other member of the receptor-ligand pair may be used for recognizing the anti-scFv antibody disclosed herein via binding between the receptor-ligand pair. In some instances, the anti-scFv antibody may be conjugated with biotin and a secondary antibody conjugated with streptavidin may be used. The secondary antibody may further be conjugated with a detectable label that releases a detectable signal directly or indirectly. The intensity of the detectable signal could be used to measure the level of the anti-CD70 scFv in a sample.

Any of the anti-scFv antibodies disclosed herein can be used for detecting and/or quantifying cells (e.g., immune cells such as T cells) that are genetically engineered to express a chimeric antigen receptor comprising the anti-CD70 scFv of SEQ ID NO:1. As used herein, a chimeric antigen receptor (CAR) refers to an artificial immune cell receptor that is engineered to recognize and bind to an antigen expressed by undesired cells, for example, disease cells such as cancer cells. A T cell that expresses a CAR polypeptide is referred to as a CAR T cell. Generally, a CAR is a fusion polypeptide comprising an extracellular domain that recognizes a target antigen (e.g., a single-chain variable fragment (scFv) of an antibody or other antibody fragment) and an intracellular domain comprising a signaling domain of the T-cell receptor (TCR) complex (e.g., CD3ζ) and, in most cases, a co-stimulatory domain. (Enblad et al., Human Gene Therapy. 2015; 26(8):498-505). A CAR construct may further comprise a hinge and transmembrane domain between the extracellular domain and the intracellular domain, as well as a signal peptide at the N-terminus for surface expression.

The anti-CD70 CAR to be detected by any of the anti-scFv antibodies discloses herein comprise the anti-CD70 scFv of SEQ ID NO:1, which can be the extracellular domain when the anti-CD70 CAR is expressed on cell surface. In addition to the anti-CD70 scFv of SEQ ID NO:1, the anti-CD70 CAR disclosed herein may comprise an intracellular domain (e.g., the signaling domain of CD3ζ), and optionally one or more co-stimulatory domains (e.g., a co-stimulatory domain of CD28 or 4-1BB). In some instances, such an anti-CD70 CAR may further comprise a transmembrane domain (e.g., a transmembrane domain of CD8a). Optionally, the anti-CD70 CAR may further comprise a hinge domain, which may comprise up to 300 amino acids (e.g., 10 to 100 amino acids, or 5 to 20 amino acids). In some embodiments, the hinge domain may be a CD8 hinge domain. Other hinge domains may be used.

Examples of anti-CD70 CARs comprising the anti-CD70 scFv of SEQ ID NO:1 can be found in WO/2019/097305 and WO2019215500, the relevant disclosures of each of which are incorporated by reference herein for the purpose and subject matter referenced herein. In specific examples, the anti-CD70 CAR may comprise the amino acid sequence of SEQ ID NO: 6 (provided in Table 4 below).

In some embodiments, any of the anti-scFv antibodies disclosed herein can be used for measuring T cells expressing an anti-CD70 CAR comprising SEQ ID NO: 1 as the extracellular domain during a manufacturing process for producing such anti-CD70 CAR T cells, for example, a manufacturing process for producing CTX130 cells. See, e.g., U.S. Provisional Application No. 62/934,999, filed on Nov. 13, 2019, the relevant disclosures of which are herein incorporated by reference for the purposes and subject matter referenced herein. CTX130 cells are a population of genetically engineered T cells expressing an anti-CD70 CAR comprising the amino acid sequence of SEQ ID NO: 6 and having disrupted endogenous TRAC and β2M genes.

In some instances, a manufacturing process for producing genetically modified T cells expressing an anti-CD70 CAR comprising the anti-CD70 scFv of SEQ ID NO: 1 (e.g., CTX130 cells) may involve enriching and activating T cells, which may be obtained from human donors, introducing genetic modifications into the T cells thus activated to produce T cells, at least a portion of which express the anti-CD70 CAR and the other desired genetic edits, depleting TCRαβ-expressing T cells from the population of genetically modified T cells thus produced, and harvesting the resultant anti-CD70 CAR-expressing T cells. See, e.g., U.S. Provisional Application No. 62/934,999, filed on Nov. 13, 2019, the relevant disclosures of which are herein incorporated by reference for the purposes and subject matter referenced herein.

To monitor such a manufacturing process for producing T cells expressing the desired anti-CD70 CAR, one or more samples may be obtained during any stage of the manufacturing process, e.g., before or after a nucleic acid encoding an anti-CD70 CAR comprising the scFv of SEQ ID NO: 1 is introduced into T cell, or both, and the amount of anti-CD70 CAR-expressing T cells in the sample may be measured according to methods described herein. For example, a fluorescent dye-conjugated anti-scFv antibody as disclosed herein may be incubated with the one or more samples under suitable conditions for a suitable period allowing for binding of the anti-scFv antibody to the cell surface-expressed anti-CD70 CAR. The presence of level of the T cells expressing the anti-CD70 CAR can then be determined via a routine method, for example, by fluorescence-activated cell sorting (FACS).

For example, after incubating T cells with components for genetically modifying the T cells (including introducing into the cells a nucleic acid encoding the desired anti-CD70 CAR), a sample containing the resultant T cells may be obtained and the anti-scFv antibodies disclosed herein may be used to detect or quantify the portion of T cells in the sample that express the anti-CD70 CAR. Alternatively, or in addition to, one or more samples comprising the genetically modified T cells may be obtained after the depleting step for removing TCRαβ T cells, after any of in vitro expansion steps after the genetic manipulation, and/or after harvesting the resultant genetically engineered T cells. The amount of anti-CD70 CAR-expressing T cells in these samples may be determined using the anti-scFv antibody disclosed herein.

In some examples, a sample may be obtained from a population of T cells genetically engineered to express the anti-CD70 CAR disclosed herein after cryopreservation and before administration to a patient. The amount of anti-CD70 CAR-expressing T cells ($CAR^+$ T cells) in the sample can be measured using the anti-scFv antibody disclosed herein to make sure that a sufficient amount of the anti-CD70 CAR-expressing T cells is given to the patient.

In some embodiments, any of the anti-scFv antibodies disclosed herein can be used for clinical assessment of T cells expressing an anti-CD70 CAR comprising the anti-CD70 scFv of SEQ ID NO:1 (e.g., the CTX130 cells) after such CAR-T cells are administered to a subject in need of the treatment, for example, for evaluating the in vivo pharmacokinetic (PK) and/or pharmacodynamic (PD) behavior of the anti-CD70 CAR T cells.

For example, one or more biological samples may be obtained from a human patient administered T cells genetically engineered to express the anti-CD70 CAR (e.g., the CTX130 cells) at one or more time points after the administration. The level of the $CAR^+$ T cells in the one or more biological samples can be measured by any of the anti-scFv antibodies disclosed herein via a conventional method, e.g., FACS. Such $CAR^+$ T cell levels, e.g., at different time point after administration, may be used to analyze PK and/or PD features of the anti-CD70 CAR-T cells in that human patient. Such CAR+ T cell levels may also be used for assessing potential treatment efficacy in that human patient.

As used herein, a "biological sample" refers to a composition that comprises tissue, e.g., blood, plasma or protein, from a subject. A biological sample can be an initial unprocessed sample taken from a subject or a subsequently processed sample, e.g., partially purified or preserved forms. In some embodiments, multiple (e.g., at least 2, 3, 4, 5, or more) biological samples may be collected from a subject, over time or at particular time intervals, for example to assess the level of T cells expressing the anti-CD70 CAR in a human patient who has been administered such T cells. Examples of biological samples include, but are not limited to, tissue, organ, blood, plasma, serum, fluid, protein, nucleic acid, skin, or a combination thereof.

The terms "patient," "subject," or "individual" may be used interchangeably and refer to a subject who needs the analysis as described herein. In some embodiments, the subject is a human patient, which has been administered a plurality of T cells, which are genetically engineered to express the anti-CD70 CAR. In some embodiments, the human patient is a cancer patient, for example, having relapsed or refractory B-cell malignancy such as non-Hodgkin lymphoma or B-cell lymphoma. In some embodiments, the human patient is a cancer patient, for example, having a CD70+ solid tumor such as a renal cell carcinoma (RCC), a lung cancer, a gastric cancer, an ovarian cancer, a pancreatic cancer, a prostate cancer, and/or a combination thereof.

In some embodiments, any of the anti-scFv antibodies disclosed herein can be used for monitoring the presence and/or the level of anti-CD70 CAR T cells in a subject during treatment. Such monitoring may be useful for assessing expansion and/or persistence of the anti-CD70 CAR T cells in the subject. In some examples, monitoring the presence and/or level of anti-CD70 CAR T cells in a subject may be useful for identifying a subject as suitable for redosing of the anti-CD70 CAR T cells and/or identifying a subject as suitable for an additional therapy.

IV. Kits for Detecting Anti-CD70 scFv of SEQ ID NO:1 and Anti-CD70 CAR Comprising Such The present disclosure also provides kits for use in detecting or quantifying a single-chain variable fragment (scFv) consisting of the amino acid sequence of SEQ ID NO: 1 in a sample, such as a sample obtained from a manufacturing process for producing anti-CD70 CAR-T cells or a sample obtained from patients who are administered anti-CD70 CAR-T cells. Such kits can include one or more containers comprising an anti-scFv antibody, e.g., any of those described herein such as antibody 20H05-02D09.

In some embodiments, the kit can comprise instructions for use in accordance with any of the methods described herein. The included instructions can comprise a description of detecting or quantifying the scFv in a sample as described herein. Instructions supplied in the kits of the invention are typically written instructions on a label or package insert (e.g., a paper sheet included in the kit), but machine-readable instructions (e.g., instructions carried on a magnetic or optical storage disk, or available via an internet address provided in the kit) are also acceptable.

The kits of this invention are in suitable packaging. Suitable packaging includes, but is not limited to, vials, bottles, jars, flexible packaging (e.g., sealed Mylar or plastic bags), and the like. The kits may comprise one or more aliquots of an anti-scFv antibody described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); Nucleic Acid Hybridization (B. D. Hames & S. J. Higgins eds. (1985; *Transcription and Translation* (B. D. Hames & S. J. Higgins, eds. (1984; *Animal Cell Culture* (R. I. Freshney, ed. (1986; *Immobilized Cells and Enzymes* (IRL Press, (1986; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described may be more fully understood, the following examples are set forth. The examples described in this application are offered to illustrate the methods and compositions provided herein and are not to be construed in any way as limiting their scope.

Example 1. Antigen Expression and Purification

This Example reports expression and purification of a His-tagged single-chain variable fragment of a mouse anti-human CD70 monoclonal antibody (anti-CD70-scFv), which was subsequently used to generate antibodies against the scFv as described in Example 2.

The anti-CD70-scFv protein comprises, from N-terminal to C-terminal, an artificial signal peptide at the N-terminus, an anti-CD70 scFv fragment consisting of the amino acid sequence of SEQ ID NO: 1, and a His-tag at the C-terminus. The amino acid sequence and the corresponding nucleic acid sequence of this anti-CD70-scFv protein are shown in SEQ ID NO: 4 and SEQ ID NO: 5, respectively. Sequences corresponding to the artificial signal peptide are underlined and the His-tag sequences are shown in bold.

(SEQ ID No: 4)
MGWSCIILFLVATATGVHSQVQLVQSGAEVKKPGASVKVSCKASGYTFTN

YGMNWVRQAPGQGLKWMGWINTYTGEPTYADAFKGRVTMTRDTSISTAYM

ELSRLRSDDTAVYYCARDYGDYGMDYWGQGTTVTVSSGGGGSGGGGSGGG

GSGDIVMTQSPDSLAVSLGERATINCRASKSVSTSGYSFMHWYQQKPGQP

PKLLIYLASNLESGVPDRFSGSGSGTDFTLTISSLQAEDVAVYYCQHSRE

VPWTFGQGTKVEIKHHHHHH

(SEQ ID No: 5)
ATGGGCTGGTCCTGCATCATTCTGTTTCTGGTGGCCACAGCCACCGGCGT

GCACTCTCAAGTTCAGCTGGTTCAGTCTGGCGCCGAAGTGAAGAAACCTG

GCGCCTCTGTGAAGGTGTCCTGCAAGGCCAGCGGCTACACCTTTACCAAC

TACGGCATGAACTGGGTCCGACAGGCTCCTGGACAGGGCCTGAAATGGAT

GGGCTGGATCAACACCTACACCGGCGAGCCTACTTACGCCGACGCCTTTA

AGGGCAGAGTGACCATGACCAGAGACACCAGCATCAGCACCGCCTACATG

GAACTGAGCCGGCTGAGATCCGATGACACCGCCGTGTACTACTGCGCCAG

AGACTACGGCGATTACGGCATGGATTATTGGGGCCAGGGCACCACCGTGA

CAGTTTCTAGCGGAGGCGGAGGATCTGGTGGCGGAGGAAGTGGCGGAGGC

GGTTCTGGCGATATCGTGATGACACAGAGCCCCGATAGCCTGGCCGTGTC

ACTGGGAGAAAGAGCCACCATCAACTGCCGGGCCAGCAAGTCTGTGTCCA

CCTCCGGCTATAGCTTCATGCACTGGTATCAGCAGAAGCCCGGCCAGCCT

CCTAAGCTGCTGATCTACCTGGCCAGCAACCTGGAAAGCGGCGTGCCCGA

TAGATTTTCTGGCAGCGGCTCTGGCACCGACTTCACCCTGACAATTAGCT

CCCTGCAGGCCGAGGATGTGGCCGTGTATTATTGCCAGCACAGCCGCGAG

GTGCCATGGACATTTGGCCAGGGAACAAAGGTGGAAATCAAGCACCACCA

CCATCACCACTGA

The DNA sequence corresponding to the anti-CD70-scFv (SEQ ID NO: 5) was subcloned into pcDNA3.4 vector, and the resulting anti-CD70-scFv DNA expression construct was transfected into Expi293F cells. One-liter of the Expi293F cells were cultured in suspension in a serum-free Expi293F™ expression medium (Thermo Fisher Scientific, Waltham, Mass., Cat. No. A1435101) to transiently express the recombinant anti-CD70-scFv protein. The cell culture supernatant was filtered and loaded onto a HisTrap® FF Crude column (GE Healthcare, Chicago, Ill., Cat. No. 17-5286-01). The expressed recombinant anti-CD70-scFv protein was purified and buffer exchanged for PBS (pH 7.2).

Figure 1B:
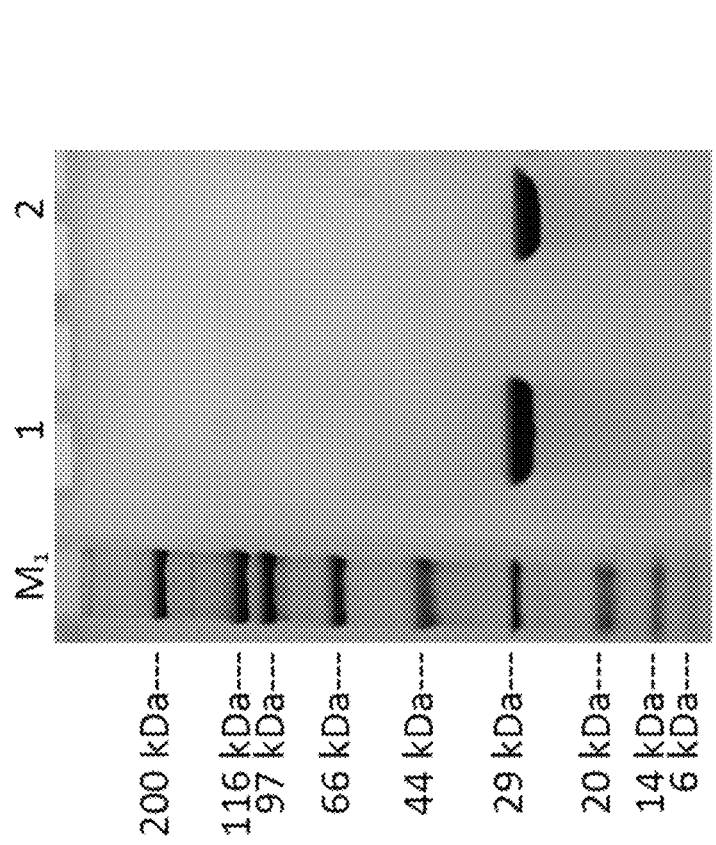

Recombinant anti-CD70-scFv protein was analyzed by SDS-PAGE and Western-blot under reducing (labeled 1 in FIGS. 1A-1B) and non-reducing (labeled 2 in FIGS. 1A-1B) conditions. The estimated molecular weight (MW) and purity of the recombinant anti-CD70-scFv protein were approximately 27 kDa and 95%, respectively. Based on Bradford protein assay, the estimated concentration and yield of the recombinant anti-CD70-scFv protein were 0.64 mg/ml and 9.60 mg, respectively. Mass spectrometry analysis was used to determine the experimental average MW of the purified recombinant anti-CD70-scFv protein. The theoretical and experimental average MWs were 29020.1 Da and 27014.8 Da, respectively. MALDI-TOF mass spectrometry was used to authenticate the amino-acid sequence of the expressed recombinant anti-CD70-scFv protein.

Example 2. Anti-CD70-scFv Antibody Generation

Immunization of mice and serum antibody titer determination was performed as described herein. Five BALB/c and five C57BL/6 mice were used for anti-CD70-scFv antibody generation. Mice were immunized with anti-CD70-scFv protein prepared in appropriate adjuvants per the schedule shown in Table 2.

TABLE 2

Animal Immunization Schedule and Doses.

| | | RIMMS | | | | Boost Bleed | Extra Immunization | Bleed | Extra Immunization | Bleed | Fusion Boost | Fusion |
|---|---|---|---|---|---|---|---|---|---|---|---|---|
| | | Immunogen | | | | | | | | | | |
| | | Anti-CD70-scFv-KLH | | | | | 1:1 mix of anti-CD70-scFv-KLH and anti-CD70-scFv | | Anti-CD70-scFv | | Anti-CD70-scFv | |
| | | Day | | | | | | | | | | |
| Mice | | 0 | 3 | 6 | 9 | 20 | 30 | 40 | 63 | 73 | 90 | 94 |
| Balb/C | #1 | 20 μg | 20 μg | 20 μg | 20 μg | Yes | 160 μg | Yes | 100 μg | Yes | | |
| | #2 | 20 μg | 20 μg | 20 μg | 20 μg | Yes | 160 μg | Yes | 100 μg | Yes | | |
| | #3 | 20 μg | 20 μg | 20 μg | 20 μg | Yes | 160 μg | Yes | 100 μg | Yes | | |
| AJ | #1 | 20 μg | 20 μg | 20 μg | 20 μg | Yes | 160 μg | Yes | 100 μg | Yes | | |
| | #2 | 20 μg | 20 μg | 20 μg | 20 μg | Yes | 160 μg | Yes | 100 μg | Yes | | |
| | #3 | 20 μg | 20 μg | 20 μg | 20 μg | Yes | 160 μg | Yes | 100 μg | Yes | 50 μg | X |

RIMMS, Repetitive Immunization Multiple Sites.

After each boost, serum was separated from the blood samples, and antibody titers were determined by indirect ELISA. The coating antigens were:

A: Recombinant anti-CD70-scFv protein;

B: Recombinant anti-BCMA-scFv protein;

C: an irrelevant His-tagged protein; and

D: Total human IgG (HuIgG).

The coating antigens were prepared in Phosphate Buffered Saline (PBS), pH 7.4, at 1 μg/ml and 100 μl/well. The secondary antibody was Peroxidase-AffiniPure Goat Anti-Mouse IgG, Fcγ fragment-specific (Jackson ImmunoResearch, West Grove, Pa., Cat. No. 115-035-071). After the third immunization, a serum sample from each mouse was also evaluated by flow cytometry.

Mice were immunized with anti-CD70-scFv according to 28-day RIMMs protocol (four 20 μg doses, 2 with adjuvant, 2 without adjuvant, delivered at 4 different sites subcutaneously). See Kilpatrick et al., Rapid Development of Affinity Matured Monoclonal Antibodies Using RIMMS. Hybridoma. Vol. 16, No. 4 (1997), the relevant disclosures of which are herein incorporated by reference for the purposes and subject matter referenced herein. Sera from the mice was assayed at day 20 with 4 concurrent ELISAs against anti-CD70-scFv, anti-BCMA-scFv, irrelevant His-tagged protein, and HuIgG. Sera from the mouse selected for fusion would have a fusion-ready titer against anti-CD70-scFv (>0.10D over background signal). Cross reactivity to anti-BCMA-scFv and His-tagged protein was expected, and therefore mice were ranked on the response differential between anti-CD70-scFv and anti-BCMA-scFv and His-tagged protein. Negative reactivity to HuIgG was preferred. The desired screening profile was not achieved on day 20. Mice were boosted on Day 30 with a 1:1 mix of anti-CD70-scFv-KLH and unconjugated anti-CD70-scFv. Sera was assayed 10 days later. However, desired screening profile was not achieved.

Mice were boosted after three weeks with anti-CD70-scFv-Fc fusion protein. Sera was assayed 10 days later. A titer ready response to anti-CD70-scFv-Fc fusion protein in all mice was establish. Cross-reactivity to anti-BCMA-scFV was seen in all mice, and a differential in the direction of antiCD70-scFV indicated a specific response existed. Cross reactivity to HuIgG was also seen. A strong response to KLH in all mice was recorded. This response indicated the RIMMS and extended boost were effective in raising an immune response. Mouse AJ #3 was chosen for cell fusion.

Mouse AJ #3 was boosted with 50 μg anti-CD70-scFv, 250 μL in saline, via intraperitoneal injection 4 days prior to spleen harvest. Harvested splenocytes were fused with FO mouse myeloma cells using a standard hybridoma protocol and the fusion products were seeded into twenty 96 well ELISA plates. Wells were screened with a triple ELISA against anti-CD70-scFv, anti-BCMA-scFv, and HuIgG ten days after plates were seeded. 51 wells were selected for scale up to 15 mL for cryopreservation. 15 mL overgrown supernatants were screened with a triple ELISA against the same three reagents. Following secondary fusion screening, 11 wells failed to maintain screening criteria. The IgG from the supernatants of the remaining 40 fusion products was purified and analyzed by FACS (Table 3).

TABLE 3

Screening of Purified IgG from Culture Supernatants Derived from Post-Fusion ELISA Positive Wells for the presence of anti-CD70 CAR Binding Antibodies by Flow Cytometry.

| # | Clone ID | % CAR positive cells |
|---|---|---|
| 1 | 01D08 | 40.5 |
| 2 | 02A05 | 37.8 |
| 3 | 04G05 | 40.4 |
| 4 | 04H09 | 39.6 |
| 5 | 05D10 | 41.4 |
| 6 | 06F03 | 39 |
| 7 | 06F12 | 46.2 |
| 8 | 07A04 | 47.2 |
| 9 | 07G07 | 42.7 |
| 10 | 08E04 | 47.2 |
| 11 | 08E05 | 42.3 |
| 12 | 09H03 | 48.4 |
| 13 | 10A06 | 0.46 |
| 14 | 10E10 | 24.3 |
| 15 | 11A11 | 40.4 |
| 16 | 11H08 | 41.9 |
| 17 | 12B03 | 41.5 |
| 18 | 12F10 | 40.2 |
| 19 | 12G11 | 3.75 |
| 20 | 13B05 | 42.3 |
| 21 | 13C10 | 40.9 |
| 22 | 13F07 | 34.9 |
| 23 | 13F09 | 26.9 |
| 24 | 14C04 | 25.3 |
| 25 | 14C09 | 44.5 |
| 26 | 14F09 | 42.6 |
| 27 | 16A08 | 30.6 |
| 28 | 16C10 | 40.8 |
| 29 | 16D03 | 41.9 |
| 30 | 16D08 | 42.4 |
| 31 | 17D11 | 3.91 |
| 32 | 17G10 | 0.34 |
| 33 | 18C08 | 37.7 |
| 34 | 19A04 | 40.9 |
| 35 | 19C12 | 41.7 |
| 36 | 19D12 | 40 |
| 37 | 20A07 | 40.7 |
| 38 | 20C05 | 29.6 |
| 39 | 20E11 | 42.7 |
| 40 | 20H05 | 41.9 |
| Negative control (isotype; mouse IgG) | | 1.24 |
| Secondary antibody only (Goat anti-mouse-AF-647) | | 1 |
| Positive control (Goat anti-mouse (GAM)-Biotin) | | 72.4 |

Based on performance (ability of clearly separate CAR positive and negative cell populations) of these purified IgGs in the flow cytometry (FACS) screen, 6 parental cell lines were selected to subclone: 07A04, 11A11, 12B03, 14F09, 20A07, and 20H05. The top 3 subclones from each parent were then selected for further screening (Table 4).

TABLE 4

Screening of Culture Supernatants from Top Three ELISA Positive Sub-clones of Six Selected Clones by Flow Cytometry Using Anti-CD70 CAR T Cells.

| # | Clone ID | Subclone ID | % CAR positive cells |
|---|---|---|---|
| 1 | 07A05 | 07A05-02B06 | 79.9 |
| | | 07A05-02B10 | 31.4 |
| | | 07A05-02C04 | 78.9 |
| 2 | 11A11 | 11A11-02C11 | 79 |
| | | 11A11-02G02 | 78 |
| | | 11A11-02H02 | 77.8 |
| 3 | 12B03 | 12B03-02D01 | 77.6 |
| | | 12B03-02D09 | 77.6 |
| | | 12B03-02E10 | 78.4 |

TABLE 4-continued

Screening of Culture Supernatants from Top Three ELISA Positive Sub-clones of Six Selected Clones by Flow Cytometry Using Anti-CD70 CAR T Cells.

| # | Clone ID | Subclone ID | % CAR positive cells |
|---|---|---|---|
| 4 | 14F09 | 14F09-02C03 | 79.1 |
|   |       | 14F09-02E04 | 77.3 |
|   |       | 14F09-02E10 | 79.6 |
| 5 | 20A07 | 20A07-02E09 | 78.8 |
|   |       | 20A07-02G04 | 77.9 |
|   |       | 20A07-02G09 | 77.6 |
| 6 | 20H05 | 20H05-02C08 | 79.4 |
|   |       | 20H05-02D07 | 80.1 |
|   |       | 20H05-02D09 | 80.1 |
| Goat anti-mouse-AF647 | | | 0.29 |
| Negative control (mouse IgG) | | | 3.83 |
| Negative culture supernatant | | | 0.84 |

Based on the above shown FACS analysis, subclone 20H05-02D09 was selected for large scale in vitro production.

A 5 liter production of subclone hybridoma cell line anti-CD70-scFv-AJ-1.3-20H05-02D09 was completed using the following media: DME/F12 with 10% Ultra Low Bovine IgG FBS, 10% NCTC-109, 2% HT, 1% Pen-Strep, 1% L-glutamine, 0.1% 1000×ITS. Antibody from the culture supernatant was purified by Protein-A column chromatography. Yield of the purified antibody was estimated to be 182.0 mg. Isotype testing indicated 20H05-02D09 to be murine IgG1, kappa type. Size Exclusion Chromatography (SEC) analysis of the protein-A purified antibody established purity at 98.9%.

The purified 20H05-02D09 antibody was analyzed by flow cytometry for binding to CAR T cells expressing the anti-CD70 CAR of SEQ ID NO: 6 (anti-CD70 CAR T cells). CAR T cells expressing an anti-BCMA CAR of SEQ ID NO: 7 (anti-BCMA CAR T cells) or an anti-CD19 CAR SEQ ID NO: 8 (anti-CD19 CAR T cells) were used as negative controls. Anti-CD70-scFv antibody (20H05-02D09) was analyzed at various dilutions (FIG. 2). The antibody was found to be highly specific to anti-CD70 CAR T cells as it bound anti-CD70 CAR T cells but did not bind either anti-BCMA CAR T cells or anti-CD19 CAR T cells over the range of antibody dilutions.

Sequences of anti-CD70 CAR (SEQ ID NO: 6), anti-BCMA CAR (SEQ ID NO: 7), and the anti-CD19 CAR (SEQ ID NO: 8) are provided in Table 5, and described in WO/2019/097305, and WO2019215500, the relevant disclosures of each of which are herein incorporated by reference for the purposes and subject matter referenced herein.

TABLE 5

CAR Sequences.

| CAR | SEQ ID NO: | Amino Acid Sequence |
|---|---|---|
| Anti-CD70 CAR | 6 | MALPVTALLLPLALLLHAARPQVQLVQSGAEVKKPGASVKV SCKASGYTFTNYGMNWVRQAPGQGLKWMGWINTYTGEPTYA DAFKGRVTMTRDTSISTAYMELSRLRSDDTAVYYCARDYGD YGMDYWGQGTTVTVSSGGGGSGGGGSGGGGSGDIVMTQSPD SLAVSLGERATINCRASKSVSTSGYSFMHWYQQKPGQPPKL LIYLASNLESGVPDRFSGSGSGTDFTLTISSLQAEDVAVYY CQHSREVPWTFGQGTKVEIKSAAAFVPVFLPAKPTTTPAPR PPTPAPTIASQPLSLRPEACRPAAGGAVHTRGLDFACDIYI WAPLAGTCGVLLLSLVITLYCNHRNRKRGRKKLLYIFKQPF MRPVQTTQEEDGCSCRFPEEEEGGCELRVKFSRSADAPAYQ QGQNQLYNELNLGRREEYDVLDKRRGRDPEMGGKPRRKNPQ EGLYNELQKDKMAEAYSEIGMKGERRRGKGHDGLYQGLSTA TKDTYDALHMQALPPR |
| Anti-BCMA CAR | 7 | MALPVTALLLPLALLLHAARPQVQLVQSGAELKKPGASVKV SCKASGNTLTNYVIHWVRQAPGQRLEWMGYILPYNDLTKYS QKFQGRVTITRDKSASTAYMELSSLRSEDTAVYYCTRWDWD GFFDPWGQGTTVTVSSGGGGSGGGGSGGGGSEIVMTQSPAT LSVSPGERASISCRASQSLVHSNGNTHLHWYQQRPGQAPRL LIYSVSNRFSEVPARFSGSGSGTDFTLTISSVESEDFAVYY CSQTSHIPYTFGGGTKLEIKSAAAFVPVFLPAKPTTTPAPR PPTPAPTIASQPLSLRPEACRPAAGGAVHTRGLDFACDIYI WAPLAGTCGVLLLSLVITLYCNHRNRKRGRKKLLYIFKQPF MRPVQTTQEEDGCSCRFPEEEEGGCELRVKFSRSADAPAYQ QGQNQLYNELNLGRREEYDVLDKRRGRDPEMGGKPRRKNPQ EGLYNELQKDKMAEAYSEIGMKGERRRGKGHDGLYQGLSTA TKDTYDALHMQALPPR |
| Anti-CD19 CAR | 8 | MLLLVTSLLLCELPHPAFLLIPDIQMTQTTSSLSASLGDRV TISCRASQDISKYLNWYQQKPDGTVKLLIYHTSRLHSGVPS RFSGSGSGTDYSLTISNLEQEDIATYFCQQGNTLPYTFGGG TKLEITGSTSGSGKPGSGEGSTKGEVKLQESGPGLVAPSQS LSVTCTVSGVSLPDYGVSWIRQPPRKGLEWLGVIWGSETTY YNSALKSRLTIIKDNSKSQVFLKMNSLQTDDTAIYYCAKHY YYGGSYAMDYWGQGTSVTVSSAAAFVPVFLPAKPTTTPAPR PPTPAPTIASQPLSLRPEACRPAAGGAVHTRGLDFACDIYI WAPLAGTCGVLLLSLVITLYCNHRNRSKRSRLLHSDYMNMT PRRPGPTRKHYQPYAPPRDFAAYRSRVKFSRSADAPAYQQG QNQLYNELNLGRREEYDVLDKRRGRDPEMGGKPRRKNPQEG LYNELQKDKMAEAYSEIGMKGERRRGKGHDGLYQGLSTATK DTYDALHMQALPPR |

The variable region of the mouse anti-CD70-scFv monoclonal antibody 20H05-02D09 was sequenced. Total RNA was isolated from the hybridoma cells using the TRIZOL® Reagent (Thermo Fisher Scientific, Waltham, Mass., Cat. No. 15596-026). cDNA was generated by reverse-transcription using the total RNA as a template and isotype-specific anti-sense primers or universal primers. The PrimeScript™ 1st Strand cDNA Synthesis Kit (Takara Bio USA, Mountain View, Calif., Cat. No. 6215A) was used according to the manufacturer's technical manual. The heavy chain and light chain sequences were amplified using rapid amplification of cDNA ends (RACE) (GenScript Biotech, Piscataway, N.J.). The amplified antibody fragments were subcloned. PCR was used to identify clones with the correct insert size. The heavy chain variable ($V_H$) domain and the light chain variable ($V_L$) domain sequences were annotated using online tools: National Center for Biotechnology Information (NCBI) Nucleotide BLAST®, IMGT/V Quest and NCBI IgBLAST®.

The heavy chain variable ($V_H$) domain and the light chain variable ($V_L$) domain sequences of the mouse anti-CD70-scFv monoclonal antibody 20H05-02D09 are provided in Table 6 (determined by the Kabat scheme or the Chothia scheme as indicated).

TABLE 6

Amino acid sequences of anti-CD70-scFv antibody 20H05-02D09.

| | | SEQ ID NO: | Amino Acid Sequence |
|---|---|---|---|
| Kabat | HCDR1 | 9 | NYGMH |
| | HCDR2 | 10 | WINTYSGVPTYPDDFK |
| | HCDR3 | 11 | ERLRGWFPF |
| Chothia | HCDR1 | 12 | GYTFTNYG |
| | HCDR2 | 13 | INTYSGVP |
| | HCDR3 | 14 | ATERLRGWFPF |
| Kabat | LCDR1 | 15 | SASSSVSYMY |
| | LCDR2 | 16 | RTSNLAS |
| | LCDR3 | 17 | QQYHSYPPT |
| Chothia | LCDR1 | 18 | SSVSY |
| | LCDR2 | None | RTS |
| | LCDR3 | 17 | QQYHSYPPT |
| Signal Peptide | $V_H$ | 19 | MHSSALLCCLVLLTGVRA |
| | $V_L$ | 19 | MHSSALLCCLVLLTGVRA |
| $V_H$ | | 2 | QIQLVQSGPELKKPGETVKISCKASGYTFTNYGMHWVKQAPG KVLKWMGWINTYSGVPTYPDDFKGRFAFSLETSASTASLQIN NLKNEDTATYFCATERLRGWFPFWGQGTLVTVSA |
| $V_L$ | | 3 | QIVLTQSPAIMSASPGEKVTISCSASSSVSYMYWYQQKPGSS PKPWIYRTSNLASGVPARFSGSGSGTSYSLTISSMEAEDAAT YYCQQYHSYPPTFGGGTKLEIK |
| $V_H$ (Including Signal Peptide, underlined) | | 20 | MHSSALLCCLVLLTGVRAQIQLVQSGPELKKPGETVKISCKA SGYTFTNYGMHWVKQAPGKVLKWMGWINTYSGVPTYPDDFKG RFAFSLETSASTASLQINNLKNEDTATYFCATERLRGWFPFW GQGTLVTVSA |
| $V_L$ (Including Signal Peptide, underlined) | | 21 | MHSSALLCCLVLLTGVRAQIVLTQSPAIMSASPGEKVTISCSAS SSVSYMYWYQQKPGSSPKPWIYRTSNLASGVPARFSGSGSGTSY SLTISSMEAEDAATYYCQQYHSYPPTFGGGTKLEIK |
| Heavy Chain | | 22 | MHSSALLCCLVLLTGVRAQIQLVQSGPELKKPGETVKISCKA SGYTFTNYGMHWVKQAPGKVLKWMGWINTYSGVPTYPDDFKG RFAFSLETSASTASLQINNLKNEDTATYFCATERLRGWFPFW GQGTLVTVSAAKTTPPSVYPLAPGSAAQTNSMVTLGCLVKGY FPEPVTVTWNSGSLSSGVHTFPAVLQSDLYTLSSSVTVPSST WPSETVTCNVAHPASSTKVDKKIVPRDCGCKPCICTVPEVSS VFIFPPKPKDVLTITLTPKVTCVVVDISKDDPEVQFSWFVDD VEVHTAQTQPREEQFNSTFRSVSELPIMHQDWLNGKEFKCRV NSAAFPAPIEKTISKTKGRPKAPQVYTIPPPKEQMAKDKVSL TCMITDFFPEDITVEWQWNGQPAENYKNTQPIMDTDGSYFVY SKLNVQKSNWEAGNTFTCSVLHEGLHNHHTEKSLSHSPGK |
| Light Chain | | 23 | MHSSALLCCLVLLTGVRAQIVLTQSPAIMSASPGEKVTISCS ASSSVSYMYWYQQKPGSSPKPWIYRTSNLASGVPARFSGSGS GTSYSLTISSMEAEDAATYYCQQYHSYPPTFGGGTKLEIKRA DAAPTVSIFPPSSEQLTSGGASVVCFLNNFYPKDINVKWKID GSERQNGVLNSWTDQDSKDSTYSMSSTLTLTKDEYERHNSYT CEATHKTSTSPIVKSFNRNEC |

Taken together, the results described herein demonstrate generation of antibodies against the scFv of mouse anti-human CD70 antibody, including generation of mouse anti-CD70-scFv monoclonal antibody 20H05-02D09.

Example 3. Large Scale Antibody Production

The 20H05-02D09 antibody was prepared in large scales using two different methods.

In the first (native) method, hybridoma cells (20H05-02D09) were cultured in low IgG culture medium in a roller bottle for 10 days. The supernatants were collected and protein A purified to obtain purified antibodies. The purified antibodies were analyzed for the ability to bind the anti-CD70-scFv protein and anti-CD70 CAR T cells using ELISA. The 20H05-02D09 antibody showed minimum cross activity to the anti-CD70-scFv linker peptide, the His tagged protein, or total human IgG.

In the second (recombinant) method, the expression vectors with the $V_H$ and $V_L$ sequences of the antibody (20H05-2D09) were transient transfected and expressed in 293F cells with chemically defined culture media. The mAb (20H05-2D09) was purified by Protein A affinity chromatography, ultrafiltration and then subjected to 0.2 micron sterile filtration to get the bulk of high purity.

The 20H05-2D09 antibodies produced using the recombinant method were compared with native 20H05-2D09 antibody for the ability to bind to the anti-CD70 CAR T cells using flow cytometry. Recombinant 20H05 antibodies demonstrated similar affinity to the anti-CD70 CAR T cells as native 20H05-2D09, when tested in a flow cytometry.

Taken together, these results demonstrate that mouse monoclonal antibody (20H05-2D09) binds with higher affinity to T cells expressing a CAR comprising an anti-CD70-scFv (anti-CD70 CAR T cells) in a flow cytometry assay.

Example 4. Measurement of Anti-CD70 CAR-Expressing Cells (a) Anti-CD70 CAR+ Cells Mixed with PBMCs Anti-CD70 CAR expressing cells were mixed with PBMCs at 0.1%, 0.5%, 1%, 5%, 10%, 25%, and 50% using serial dilution. The percentage of CAR+ cells in the mixed cell population was evaluated using flow cytometry in technical duplicates using an exemplary anti-CD70 CAR anti-idiotypic antibody, 20H05-02D09, at 1:3000 dilution.

Figure 3:
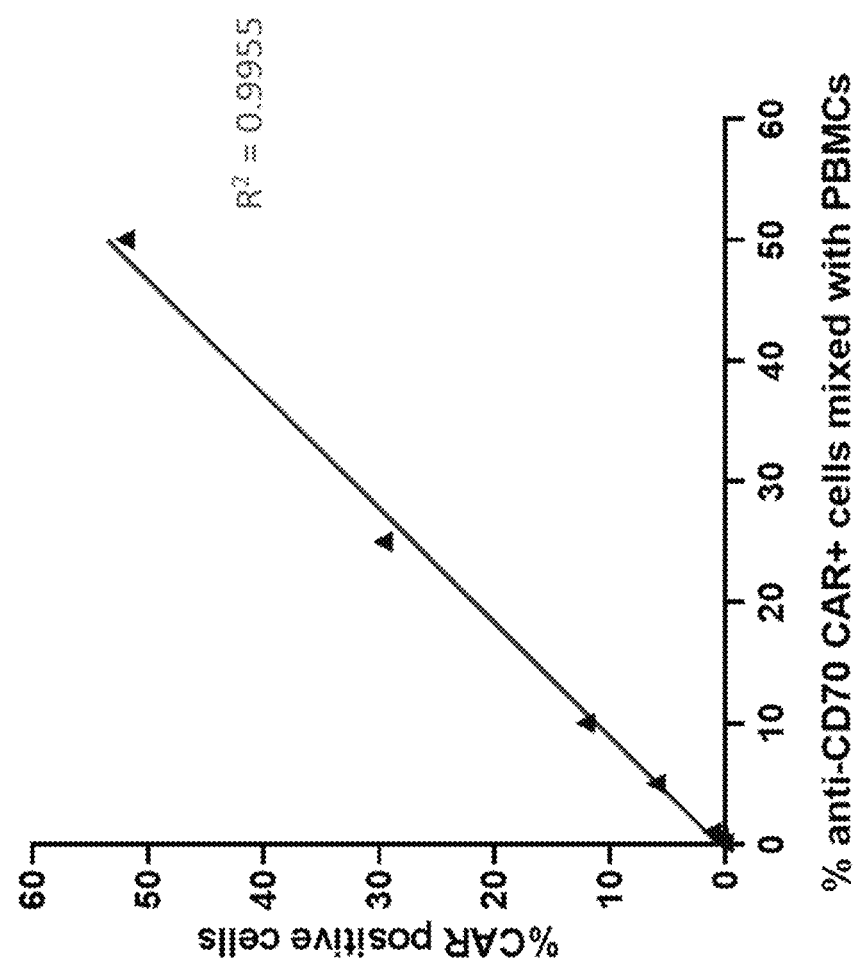
FIG. 3 is a diagram showing use of an exemplary anti-idiotype antibody, 20H05-02D09, to measure blood samples containing anti-CD70 CAR-expressing T cells.

As shown in FIG. 3, the percentage of CAR+ cells measured by flow was highly correlated to the percentage of anti-CD70 CAR expressing cells mixed in PBMC (coefficient of correlation of 0.9955) suggesting that the anti-CD70 CAR anti-idiotypic antibody allows the detection and the quantification of CAR+ cells when mixed with PBMCs. See also Table 7 below.

TABLE 7

| Percentage of CAR+ Cells | | |
|---|---|---|
| % CAR+ cells mixed with PBMCs | % CAR+ cells Replicate 1 | % CAR+ cells Replicate 2 |
| 1 | 0.028 | 0.012 |
| 0.1 | 0.15 | 0.12 |
| 0.5 | 0.62 | 0.56 |
| 1 | 1.21 | 1.16 |
| 5 | 6.03 | 6.02 |
| 10 | 12.3 | 12 |
| 25 | 29.7 | 29.7 |
| 50 | 52.3 | 51.8 |

The anti-idiotype antibody effectively detects and quantifies anti-CD70 CAR expressing cells in PMBCs, even when highly diluted (e.g., 0.1%). These results indicate that the anti-CD70 CAR idiotypic antibodies disclosed herein can be used to measure levels of the anti-CD70 CAR-expressing cells in blood samples.

(b) Measuring Anti-CD70 CAR+ Cells with Conjugated Antibody

Next, measurements of anti-CD70 CAR+ cells with the anti-idiotype antibody 20H05, unconjugated, conjugated with biotin, or conjugated with APC (allophycocyanin), were investigated following the methods disclosed above, using a cell population containing about 65.4% anti-CD70 CAR+ cells. The results are provided in Table 8 below.

TABLE 8

| Percentage of Anti-CD70 CAR+ Cells Using Unconjugated or Conjugated 20H05 | | | | | | | | |
|---|---|---|---|---|---|---|---|---|
| | Antibody Dilution | | | | | | | |
| | 1:50 | 1:100 | 1:200 | 1:400 | 1:800 | 1:1600 | 1:3200 | 1:6400 |
| Unconjugated | 67.7% | 67.5% | 68.3% | 67.2% | 66.5% | 65.4% | 67.8% | 66.5% |
| Biotin Conjugated | 66.3% | 65.9% | 67.6% | 66.4% | 67.0% | 66.4% | 66.2% | 65.3% |
| APC Conjugated | 60.8% | 61.3% | 61.7% | 61.8% | 61.5% | 61.4% | 62.7% | 62.4% |

The results showed that the APC conjugated antibody showed more than a 10% reduction in positivity and less effective separation of positive and negative populations compared to the biotin conjugated antibody. In sum, the results show that biotin-conjugated 20H05 showed more accurate results as compared with direct APC conjugated antibody.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An isolated antibody, which binds a single-chain variable fragment (scFv) consisting of the amino acid sequence of SEQ ID NO: 1, wherein the antibody comprises heavy chain complementary determining region (CDR)1, CDR2, and CDR3 comprising the amino acid sequences of SEQ ID NOs:9-11, respectively, and light chain CDR1, CDR2, and CDR3 comprising the amino acid sequences SEQ ID NOs: 15-17, respectively, following the Kabat approach.

2. The isolated antibody of claim 1, wherein the antibody binds the scFv expressed on a cell surface.

3. The isolated antibody of claim 1, which comprises a heavy chain variable region ($V_H$) comprising the amino acid sequence of SEQ ID NO:2 and a light chain variable region ($V_L$) comprising the amino acid sequence of SEQ ID NO:3.

4. The isolated antibody of claim 1, wherein the antibody is a full-length antibody or an antigen-binding fragment thereof.

5. The isolated antibody of claim 3, which comprises a heavy chain comprising the amino acid sequence of SEQ ID NO:22 and a light chain comprising the amino acid sequence of SEQ ID NO:23.

6. A method for detecting or quantifying a single-chain variable fragment (scFv) that consists of the amino acid sequence of SEQ ID NO: 1 in a sample, the method comprising:
 (i) contacting an antibody of claim 1 with a sample suspected of containing the scFv, and
 (ii) detecting binding of the antibody to the scFv, wherein the scFv is the extracellular domain of an anti-CD70 chimeric antigen receptor (CAR) expressed on a cell surface.

7. The method of claim 6, wherein the antibody is conjugated to a detectable label.

8. The method of claim 6, wherein the antibody is conjugated to biotin.

9. The method of claim 6, wherein step (ii) comprises a secondary antibody.

10. The method of claim 6, wherein the sample comprises a plurality of T cells, which are genetically engineered to express the anti-CD70 CAR.

11. The method of claim 10, wherein the plurality of T cells are prepared from T cells obtained from one or more donors.

12. The method of claim 10, wherein the sample is obtained from a process for producing a plurality of T cells, which are genetically engineered to express the anti-CD70 CAR.

13. The method of claim 10, wherein the sample is a biological sample obtained from a subject administered a plurality of T cells, which are genetically engineered to express the anti-CD70 CAR.

14. The method of claim 13, wherein the biological sample is a blood sample or a tissue sample.

15. The method of claim 13, wherein the subject is a human cancer patient.

16. The method of claim 15, wherein the human cancer patient has a relapsed or refractory B-cell malignancy.

17. The method of claim 16, wherein the relapsed or refractory B-cell malignancy is non-Hodgkin lymphoma or B-cell lymphoma.

18. The method of claim 17, wherein the human cancer patient has a CD70+ solid tumor.

19. The method of claim 18, wherein the CD70+ solid tumor is a renal cell carcinoma (RCC), a lung cancer, a gastric cancer, an ovarian cancer, a pancreatic cancer, a prostate cancer, and/or a combination thereof.

20. The method of claim 9, wherein the plurality of T cells comprise a disrupted TRAC gene, a disrupted β2M gene, or both.

* * * * *

SEQUENCE LISTING

<160> NUMBER OF SEQ ID NOS: 23

<210> SEQ ID NO 1
<211> LENGTH: 245
<212> TYPE: PRT
<213> ORGANISM: Artificial Sequence
<220> FEATURE:
<223> OTHER INFORMATION: Synthetic

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Asp Ile Val Met Thr Gln Ser Pro Asp Ser
    130                 135                 140

Leu Ala Val Ser Leu Gly Glu Arg Ala Thr Ile Asn Cys Arg Ala Ser
145                 150                 155                 160

Lys Ser Val Ser Thr Ser Gly Tyr Ser Phe Met His Trp Tyr Gln Gln
                165                 170                 175

Lys Pro Gly Gln Pro Pro Lys Leu Leu Ile Tyr Leu Ala Ser Asn Leu
            180                 185                 190

Glu Ser Gly Val Pro Asp Arg Phe Ser Gly Ser Gly Ser Gly Thr Asp
        195                 200                 205

Phe Thr Leu Thr Ile Ser Ser Leu Gln Ala Glu Asp Val Ala Val Tyr
    210                 215                 220

Tyr Cys Gln His Ser Arg Glu Val Pro Trp Thr Phe Gly Gln Gly Thr
225                 230                 235                 240

Lys Val Glu Ile Lys
                245

<210> SEQ ID NO 2
<211> LENGTH: 118
<212> TYPE: PRT
<213> ORGANISM: Artificial Sequence
<220> FEATURE:
<223> OTHER INFORMATION: Synthetic

<400> SEQUENCE: 2

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met His Trp Val Lys Gln Ala Pro Gly Lys Val Leu Lys Trp Met
        35                  40                  45

Gly Trp Ile Asn Thr Tyr Ser Gly Val Pro Thr Tyr Pro Asp Asp Phe
            50                  55                  60

Lys Gly Arg Phe Ala Phe Ser Leu Glu Thr Ser Ala Ser Thr Ala Ser
 65                  70                  75                  80

Leu Gln Ile Asn Asn Leu Lys Asn Glu Asp Thr Ala Thr Tyr Phe Cys
                    85                  90                  95

Ala Thr Glu Arg Leu Arg Gly Trp Phe Pro Phe Trp Gly Gln Gly Thr
                100                 105                 110

Leu Val Thr Val Ser Ala
            115

<210> SEQ ID NO 3
<211> LENGTH: 106
<212> TYPE: PRT
<213> ORGANISM: Artificial Sequence
<220> FEATURE:
<223> OTHER INFORMATION: Synthetic

<400> SEQUENCE: 3

Gln Ile Val Leu Thr Gln Ser Pro Ala Ile Met Ser Ala Ser Pro Gly
 1               5                  10                  15

Glu Lys Val Thr Ile Ser Cys Ser Ala Ser Ser Val Ser Tyr Met
                20                  25                  30

Tyr Trp Tyr Gln Gln Lys Pro Gly Ser Ser Pro Lys Pro Trp Ile Tyr
                35                  40                  45

Arg Thr Ser Asn Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Tyr His Ser Tyr Pro Pro Thr
                85                  90                  95

Phe Gly Gly Gly Thr Lys Leu Glu Ile Lys
                100                 105

<210> SEQ ID NO 4
<211> LENGTH: 270
<212> TYPE: PRT
<213> ORGANISM: Artificial Sequence
<220> FEATURE:
<223> OTHER INFORMATION: Synthetic

<400> SEQUENCE: 4

Met Gly Trp Ser Cys Ile Ile Leu Phe Leu Val Ala Thr Ala Thr Gly
 1               5                  10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
                35                  40                  45

Thr Asn Tyr Gly Met Asn Trp Val Arg Gln Ala Pro Gly Gln Gly Leu
 50                  55                  60

Lys Trp Met Gly Trp Ile Asn Thr Tyr Thr Gly Glu Pro Thr Tyr Ala
 65                  70                  75                  80

Asp Ala Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
                100                 105                 110

Tyr Tyr Cys Ala Arg Asp Tyr Gly Asp Tyr Gly Met Asp Tyr Trp Gly
                115                 120                 125

```
Gln Gly Thr Thr Val Thr Val Ser Ser Gly Gly Gly Ser Gly Gly
    130                 135                 140
Gly Gly Ser Gly Gly Gly Ser Gly Asp Ile Val Met Thr Gln Ser
145                 150                 155                 160
Pro Asp Ser Leu Ala Val Ser Leu Gly Glu Arg Ala Thr Ile Asn Cys
                165                 170                 175
Arg Ala Ser Lys Ser Val Ser Thr Ser Gly Tyr Ser Phe Met His Trp
            180                 185                 190
Tyr Gln Gln Lys Pro Gly Gln Pro Pro Lys Leu Leu Ile Tyr Leu Ala
        195                 200                 205
Ser Asn Leu Glu Ser Gly Val Pro Asp Arg Phe Ser Gly Ser Gly Ser
    210                 215                 220
Gly Thr Asp Phe Thr Leu Thr Ile Ser Ser Leu Gln Ala Glu Asp Val
225                 230                 235                 240
Ala Val Tyr Tyr Cys Gln His Ser Arg Glu Val Pro Trp Thr Phe Gly
                245                 250                 255
Gln Gly Thr Lys Val Glu Ile Lys His His His His His
            260                 265                 270
```

```
<210> SEQ ID NO 5
<211> LENGTH: 813
<212> TYPE: DNA
<213> ORGANISM: Artificial Sequence
<220> FEATURE:
<223> OTHER INFORMATION: Synthetic

<400> SEQUENCE: 5
atgggctggt cctgcatcat tctgtttctg gtggccacag ccaccggcgt gcactctcaa      60
gttcagctgg ttcagtctgg cgccgaagtg aagaaacctg cgcctctgt gaaggtgtcc     120
tgcaaggcca gcggctacac ctttaccaac tacggcatga actgggtccg acaggctcct     180
ggacagggcc tgaaatggat gggctggatc aacacctaca ccggcgagcc tacttacgcc     240
gacgccttta agggcagagt gaccatgacc agagacacca gcatcagcac cgcctacatg     300
gaactgagcc ggctgagatc cgatgacacc gccgtgtact actgcgccag agactacggc     360
gattacggca tggattattg gggccagggc accaccgtga cagtttctag cggaggcgga     420
ggatctggtg gcgaggaag tggcggaggc ggttctggcg atatcgtgat gacacagagc     480
cccgatagcc tggccgtgtc actgggagaa agagccacca tcaactgccg ggccagcaag     540
tctgtgtcca cctccggcta tagcttcatg cactggtatc agcagaagcc cggccagcct     600
cctaagctgc tgatctacct ggccagcaac ctggaaagcg gcgtgcccga tagattttct     660
ggcagcggct ctggcaccga cttcaccctg acaattagct ccctgcaggc cgaggatgtg     720
gccgtgtatt attgccagca cagccgcgag gtgccatgga catttggcca gggaacaaag     780
gtggaaatca agcaccacca ccatcaccac tga                                 813

<210> SEQ ID NO 6
<211> LENGTH: 508
<212> TYPE: PRT
<213> ORGANISM: Artificial Sequence
<220> FEATURE:
<223> OTHER INFORMATION: Synthetic

<400> SEQUENCE: 6
```

```
Met Ala Leu Pro Val Thr Ala Leu Leu Leu Pro Leu Ala Leu Leu Leu
1               5                   10                  15
```

```
His Ala Ala Arg Pro Gln Val Gln Leu Val Gln Ser Gly Ala Glu Val
             20                  25                  30
Lys Lys Pro Gly Ala Ser Val Lys Val Ser Cys Lys Ala Ser Gly Tyr
         35                  40                  45
Thr Phe Thr Asn Tyr Gly Met Asn Trp Val Arg Gln Ala Pro Gly Gln
     50                  55                  60
Gly Leu Lys Trp Met Gly Trp Ile Asn Thr Tyr Thr Gly Glu Pro Thr
 65                  70                  75                  80
Tyr Ala Asp Ala Phe Lys Gly Arg Val Thr Met Thr Arg Asp Thr Ser
                 85                  90                  95
Ile Ser Thr Ala Tyr Met Glu Leu Ser Arg Leu Arg Ser Asp Asp Thr
            100                 105                 110
Ala Val Tyr Tyr Cys Ala Arg Asp Tyr Gly Asp Tyr Gly Met Asp Tyr
        115                 120                 125
Trp Gly Gln Gly Thr Thr Val Thr Val Ser Ser Gly Gly Gly Gly Ser
    130                 135                 140
Gly Gly Gly Gly Ser Gly Gly Gly Gly Ser Gly Asp Ile Val Met Thr
145                 150                 155                 160
Gln Ser Pro Asp Ser Leu Ala Val Ser Leu Gly Glu Arg Ala Thr Ile
                165                 170                 175
Asn Cys Arg Ala Ser Lys Ser Val Ser Thr Ser Gly Tyr Ser Phe Met
            180                 185                 190
His Trp Tyr Gln Gln Lys Pro Gly Gln Pro Pro Lys Leu Leu Ile Tyr
        195                 200                 205
Leu Ala Ser Asn Leu Glu Ser Gly Val Pro Asp Arg Phe Ser Gly Ser
    210                 215                 220
Gly Ser Gly Thr Asp Phe Thr Leu Thr Ile Ser Ser Leu Gln Ala Glu
225                 230                 235                 240
Asp Val Ala Val Tyr Tyr Cys Gln His Ser Arg Glu Val Pro Trp Thr
                245                 250                 255
Phe Gly Gln Gly Thr Lys Val Glu Ile Lys Ser Ala Ala Ala Phe Val
            260                 265                 270
Pro Val Phe Leu Pro Ala Lys Pro Thr Thr Thr Pro Ala Pro Arg Pro
        275                 280                 285
Pro Thr Pro Ala Pro Thr Ile Ala Ser Gln Pro Leu Ser Leu Arg Pro
    290                 295                 300
Glu Ala Cys Arg Pro Ala Ala Gly Gly Ala Val His Thr Arg Gly Leu
305                 310                 315                 320
Asp Phe Ala Cys Asp Ile Tyr Ile Trp Ala Pro Leu Ala Gly Thr Cys
                325                 330                 335
Gly Val Leu Leu Leu Ser Leu Val Ile Thr Leu Tyr Cys Asn His Arg
            340                 345                 350
Asn Arg Lys Arg Gly Arg Lys Lys Leu Leu Tyr Ile Phe Lys Gln Pro
        355                 360                 365
Phe Met Arg Pro Val Gln Thr Thr Gln Glu Glu Asp Gly Cys Ser Cys
    370                 375                 380
Arg Phe Pro Glu Glu Glu Glu Gly Gly Cys Glu Leu Arg Val Lys Phe
385                 390                 395                 400
Ser Arg Ser Ala Asp Ala Pro Ala Tyr Gln Gln Gly Gln Asn Gln Leu
                405                 410                 415
Tyr Asn Glu Leu Asn Leu Gly Arg Arg Glu Glu Tyr Asp Val Leu Asp
            420                 425                 430
Lys Arg Arg Gly Arg Asp Pro Glu Met Gly Gly Lys Pro Arg Arg Lys
```

```
                    435                 440                 445
Asn Pro Gln Glu Gly Leu Tyr Asn Glu Leu Gln Lys Asp Lys Met Ala
450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                    485                 490                 495

Tyr Asp Ala Leu His Met Gln Ala Leu Pro Pro Arg
                500                 505

<210> SEQ ID NO 7
<211> LENGTH: 508
<212> TYPE: PRT
<213> ORGANISM: Artificial Sequence
<220> FEATURE:
<223> OTHER INFORMATION: Synthetic

<400> SEQUENCE: 7

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Leu
                20                  25                  30

Lys Lys Pro Gly Ala Ser Val Lys Val Ser Cys Lys Ala Ser Gly Asn
            35                  40                  45

Thr Leu Thr Asn Tyr Val Ile His Trp Val Arg Gln Ala Pro Gly Gln
        50                  55                  60

Arg Leu Glu Trp Met Gly Tyr Ile Leu Pro Tyr Asn Asp Leu Thr Lys
65                  70                  75                  80

Tyr Ser Gln Lys Phe Gln Gly Arg Val Thr Ile Thr Arg Asp Lys Ser
                85                  90                  95

Ala Ser Thr Ala Tyr Met Glu Leu Ser Ser Leu Arg Ser Glu Asp Thr
            100                 105                 110

Ala Val Tyr Tyr Cys Thr Arg Trp Asp Trp Asp Gly Phe Phe Asp Pro
        115                 120                 125

Trp Gly Gln Gly Thr Thr Val Thr Val Ser Ser Gly Gly Gly Gly Ser
130                 135                 140

Gly Gly Gly Gly Ser Gly Gly Gly Ser Glu Ile Val Met Thr Gln
145                 150                 155                 160

Ser Pro Ala Thr Leu Ser Val Ser Pro Gly Glu Arg Ala Ser Ile Ser
                165                 170                 175

Cys Arg Ala Ser Gln Ser Leu Val His Ser Asn Gly Asn Thr His Leu
            180                 185                 190

His Trp Tyr Gln Gln Arg Pro Gly Gln Ala Pro Arg Leu Leu Ile Tyr
        195                 200                 205

Ser Val Ser Asn Arg Phe Ser Glu Val Pro Ala Arg Phe Ser Gly Ser
210                 215                 220

Gly Ser Gly Thr Asp Phe Thr Leu Thr Ile Ser Ser Val Glu Ser Glu
225                 230                 235                 240

Asp Phe Ala Val Tyr Tyr Cys Ser Gln Thr Ser His Ile Pro Tyr Thr
                245                 250                 255

Phe Gly Gly Gly Thr Lys Leu Glu Ile Lys Ser Ala Ala Ala Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
```

```
              290                 295                 300
Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Arg Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

<210> SEQ ID NO 8
<211> LENGTH: 506
<212> TYPE: PRT
<213> ORGANISM: Artificial Sequence
<220> FEATURE:
<223> OTHER INFORMATION: Synthetic

<400> SEQUENCE: 8

Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
                20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
        50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
```

```
            145                 150                 155                 160

Pro Ser Gln Ser Leu Ser Val Thr Cys Thr Val Ser Gly Val Ser Leu
                    165                 170                 175

Pro Asp Tyr Gly Val Ser Trp Ile Arg Gln Pro Pro Arg Lys Gly Leu
                180                 185                 190

Glu Trp Leu Gly Val Ile Trp Gly Ser Glu Thr Thr Tyr Tyr Asn Ser
                195                 200                 205

Ala Leu Lys Ser Arg Leu Thr Ile Ile Lys Asp Asn Ser Lys Ser Gln
                210                 215                 220

Val Phe Leu Lys Met Asn Ser Leu Gln Thr Asp Asp Thr Ala Ile Tyr
    225                 230                 235                 240

Tyr Cys Ala Lys His Tyr Tyr Gly Gly Ser Tyr Ala Met Asp Tyr
                    245                 250                 255

Trp Gly Gln Gly Thr Ser Val Thr Val Ser Ser Ala Ala Ala Phe Val
                    260                 265                 270

Pro Val Phe Leu Pro Ala Lys Pro Thr Thr Thr Pro Ala Pro Arg Pro
                    275                 280                 285

Pro Thr Pro Ala Pro Thr Ile Ala Ser Gln Pro Leu Ser Leu Arg Pro
                290                 295                 300

Glu Ala Cys Arg Pro Ala Ala Gly Gly Ala Val His Thr Arg Gly Leu
    305                 310                 315                 320

Asp Phe Ala Cys Asp Ile Tyr Ile Trp Ala Pro Leu Ala Gly Thr Cys
                    325                 330                 335

Gly Val Leu Leu Leu Ser Leu Val Ile Thr Leu Tyr Cys Asn His Arg
                340                 345                 350

Asn Arg Ser Lys Arg Ser Arg Leu Leu His Ser Asp Tyr Met Asn Met
                355                 360                 365

Thr Pro Arg Arg Pro Gly Pro Thr Arg Lys His Tyr Gln Pro Tyr Ala
                370                 375                 380

Pro Pro Arg Asp Phe Ala Ala Tyr Arg Ser Arg Val Lys Phe Ser Arg
    385                 390                 395                 400

Ser Ala Asp Ala Pro Ala Tyr Gln Gln Gly Gln Asn Gln Leu Tyr Asn
                    405                 410                 415

Glu Leu Asn Leu Gly Arg Arg Glu Glu Tyr Asp Val Leu Asp Lys Arg
                420                 425                 430

Arg Gly Arg Asp Pro Glu Met Gly Gly Lys Pro Arg Arg Lys Asn Pro
                435                 440                 445

Gln Glu Gly Leu Tyr Asn Glu Leu Gln Lys Asp Lys Met Ala Glu Ala
                450                 455                 460

Tyr Ser Glu Ile Gly Met Lys Gly Glu Arg Arg Arg Gly Lys Gly His
    465                 470                 475                 480

Asp Gly Leu Tyr Gln Gly Leu Ser Thr Ala Thr Lys Asp Thr Tyr Asp
                    485                 490                 495

Ala Leu His Met Gln Ala Leu Pro Pro Arg
                    500                 505

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Asn Tyr Gly Met His
```

```
1               5

<210> SEQ ID NO 10
<211> LENGTH: 16
<212> TYPE: PRT
<213> ORGANISM: Artificial Sequence
<220> FEATURE:
<223> OTHER INFORMATION: Synthetic

<400> SEQUENCE: 10

Trp Ile Asn Thr Tyr Ser Gly Val Pro Thr Tyr Pro Asp Asp Phe Lys
1               5                   10                  15

<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Glu Arg Leu Arg Gly Trp Phe Pro Phe
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Gly Tyr Thr Phe Thr Asn Tyr Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13

Ile Asn Thr Tyr Ser Gly Val Pro
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Ala Thr Glu Arg Leu Arg Gly Trp Phe Pro Phe
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic

<400> SEQUENCE: 15

Ser Ala Ser Ser Ser Val Ser Tyr Met Tyr
1               5                   10
```

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Arg Thr Ser Asn Leu Ala Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Gln Gln Tyr His Ser Tyr Pro Pro Thr
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic

<400> SEQUENCE: 18

Ser Ser Val Ser Tyr
1               5

<210> SEQ ID NO 19
<211> LENGTH: 18
<212> TYPE: PRT
<213> ORGANISM: Artificial Sequence
<220> FEATURE:
<223> OTHER INFORMATION: Synthetic

<400> SEQUENCE: 19

Met His Ser Ser Ala Leu Leu Cys Cys Leu Val Leu Leu Thr Gly Val
1               5                   10                  15

Arg Ala

<210> SEQ ID NO 20
<211> LENGTH: 136
<212> TYPE: PRT
<213> ORGANISM: Artificial Sequence
<220> FEATURE:
<223> OTHER INFORMATION: Synthetic

<400> SEQUENCE: 20

Met His Ser Ser Ala Leu Leu Cys Cys Leu Val Leu Leu Thr Gly Val
1               5                   10                  15

Arg Ala Gln Ile Gln Leu Val Gln Ser Gly Pro Glu Leu Lys Lys Pro
            20                  25                  30

Gly Glu Thr Val Lys Ile Ser Cys Lys Ala Ser Gly Tyr Thr Phe Thr
        35                  40                  45

Asn Tyr Gly Met His Trp Val Lys Gln Ala Pro Gly Lys Val Leu Lys
    50                  55                  60

Trp Met Gly Trp Ile Asn Thr Tyr Ser Gly Val Pro Thr Tyr Pro Asp
65                  70                  75                  80

```
Asp Phe Lys Gly Arg Phe Ala Phe Ser Leu Glu Thr Ser Ala Ser Thr
                85                  90                  95

Ala Ser Leu Gln Ile Asn Asn Leu Lys Asn Glu Asp Thr Ala Thr Tyr
            100                 105                 110

Phe Cys Ala Thr Glu Arg Leu Arg Gly Trp Phe Pro Phe Trp Gly Gln
        115                 120                 125

Gly Thr Leu Val Thr Val Ser Ala
        130             135

<210> SEQ ID NO 21
<211> LENGTH: 124
<212> TYPE: PRT
<213> ORGANISM: Artificial Sequence
<220> FEATURE:
<223> OTHER INFORMATION: Synthetic

<400> SEQUENCE: 21

Met His Ser Ser Ala Leu Leu Cys Cys Leu Val Leu Leu Thr Gly Val
1               5                   10                  15

Arg Ala Gln Ile Val Leu Thr Gln Ser Pro Ala Ile Met Ser Ala Ser
            20                  25                  30

Pro Gly Glu Lys Val Thr Ile Ser Cys Ser Ala Ser Ser Val Ser
        35                  40                  45

Tyr Met Tyr Trp Tyr Gln Gln Lys Pro Gly Ser Ser Pro Lys Pro Trp
    50                  55                  60

Ile Tyr Arg Thr Ser Asn Leu Ala Ser Gly Val Pro Ala Arg Phe Ser
65                  70                  75                  80

Gly Ser Gly Ser Gly Thr Ser Tyr Ser Leu Thr Ile Ser Ser Met Glu
                85                  90                  95

Ala Glu Asp Ala Ala Thr Tyr Tyr Cys Gln Gln Tyr His Ser Tyr Pro
            100                 105                 110

Pro Thr Phe Gly Gly Gly Thr Lys Leu Glu Ile Lys
        115                 120

<210> SEQ ID NO 22
<211> LENGTH: 460
<212> TYPE: PRT
<213> ORGANISM: Artificial Sequence
<220> FEATURE:
<223> OTHER INFORMATION: Synthetic

<400> SEQUENCE: 22

Met His Ser Ser Ala Leu Leu Cys Cys Leu Val Leu Leu Thr Gly Val
1               5                   10                  15

Arg Ala Gln Ile Gln Leu Val Gln Ser Gly Pro Glu Leu Lys Lys Pro
            20                  25                  30

Gly Glu Thr Val Lys Ile Ser Cys Lys Ala Ser Gly Tyr Thr Phe Thr
        35                  40                  45

Asn Tyr Gly Met His Trp Val Lys Gln Ala Pro Gly Lys Val Leu Lys
    50                  55                  60

Trp Met Gly Trp Ile Asn Thr Tyr Ser Gly Val Pro Thr Tyr Pro Asp
65                  70                  75                  80

Asp Phe Lys Gly Arg Phe Ala Phe Ser Leu Glu Thr Ser Ala Ser Thr
                85                  90                  95

Ala Ser Leu Gln Ile Asn Asn Leu Lys Asn Glu Asp Thr Ala Thr Tyr
            100                 105                 110

Phe Cys Ala Thr Glu Arg Leu Arg Gly Trp Phe Pro Phe Trp Gly Gln
```

```
            115                 120                 125
Gly Thr Leu Val Thr Val Ser Ala Ala Lys Thr Thr Pro Pro Ser Val
        130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
    450                 455                 460

<210> SEQ ID NO 23
<211> LENGTH: 231
<212> TYPE: PRT
<213> ORGANISM: Artificial Sequence
<220> FEATURE:
<223> OTHER INFORMATION: Synthetic

<400> SEQUENCE: 23

Met His Ser Ser Ala Leu Leu Cys Cys Leu Val Leu Leu Thr Gly Val
1               5                   10                  15

Arg Ala Gln Ile Val Leu Thr Gln Ser Pro Ala Ile Met Ser Ala Ser
```

```
                    20                  25                  30
Pro Gly Glu Lys Val Thr Ile Ser Cys Ser Ala Ser Ser Ser Val Ser
        35                  40                  45

Tyr Met Tyr Trp Tyr Gln Gln Lys Pro Gly Ser Ser Pro Lys Pro Trp
    50                  55                  60

Ile Tyr Arg Thr Ser Asn Leu Ala Ser Gly Val Pro Ala Arg Phe Ser
65                  70                  75                  80

Gly Ser Gly Ser Gly Thr Ser Tyr Ser Leu Thr Ile Ser Ser Met Glu
                85                  90                  95

Ala Glu Asp Ala Ala Thr Tyr Tyr Cys Gln Gln Tyr His Ser Tyr Pro
            100                 105                 110

Pro Thr Phe Gly Gly Gly Thr Lys Leu Glu Ile Lys Arg Ala Asp Ala
        115                 120                 125

Ala Pro Thr Val Ser Ile Phe Pro Pro Ser Ser Glu Gln Leu Thr Ser
    130                 135                 140

Gly Gly Ala Ser Val Val Cys Phe Leu Asn Asn Phe Tyr Pro Lys Asp
145                 150                 155                 160

Ile Asn Val Lys Trp Lys Ile Asp Gly Ser Glu Arg Gln Asn Gly Val
                165                 170                 175

Leu Asn Ser Trp Thr Asp Gln Asp Ser Lys Asp Ser Thr Tyr Ser Met
            180                 185                 190

Ser Ser Thr Leu Thr Leu Thr Lys Asp Glu Tyr Glu Arg His Asn Ser
        195                 200                 205

Tyr Thr Cys Glu Ala Thr His Lys Thr Ser Thr Ser Pro Ile Val Lys
    210                 215                 220

Ser Phe Asn Arg Asn Glu Cys
225                 230
```